(12) United States Patent
Muratoglu et al.

(10) Patent No.: US 9,394,384 B2
(45) Date of Patent: Jul. 19, 2016

(54) TOUGH HYDROGELS

(75) Inventors: Orhun K. Muratoglu, Cambridge, MA (US); Jeeyoung Choi, Cambridge, MA (US); Hatice Bodugoz-Senturk, Boston, MA (US); Gavin J. C. Braithwaite, Cambridge, MA (US); Stephen H. Spiegelberg, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 1307 days.

(21) Appl. No.: 11/916,703

(22) PCT Filed: Sep. 27, 2005

(86) PCT No.: PCT/US2005/034662
§ 371 (c)(1),
(2), (4) Date: Jan. 18, 2008

(87) PCT Pub. No.: WO2006/132661
PCT Pub. Date: Dec. 14, 2006

(65) Prior Publication Data
US 2008/0208347 A1    Aug. 28, 2008

Related U.S. Application Data

(60) Provisional application No. 60/687,317, filed on Jun. 6, 2005, provisional application No. 60/702,279, filed on Jul. 26, 2005.

(51) Int. Cl.
*A61F 2/30* (2006.01)
*A61F 2/32* (2006.01)
*A61L 31/04* (2006.01)
*C08F 6/10* (2006.01)
*A61L 27/52* (2006.01)
*C08J 3/075* (2006.01)
*C08L 29/04* (2006.01)
*A61F 2/38* (2006.01)
*C08L 71/02* (2006.01)

(52) U.S. Cl.
CPC . *C08F 6/10* (2013.01); *A61L 27/52* (2013.01); *C08J 3/075* (2013.01); *C08L 29/04* (2013.01); *A61F 2/30756* (2013.01); *A61F 2/32* (2013.01); *A61F 2/38* (2013.01); *A61F 2/3804* (2013.01); *A61F 2002/30754* (2013.01); *C08J 2329/04* (2013.01); *C08L 71/02* (2013.01)

(58) Field of Classification Search
CPC ............ A61L 27/52; C08F 6/10; C08J 3/075; C08L 29/04
USPC .......... 522/150; 524/173, 356, 377, 379, 557, 524/916; 525/56, 61
See application file for complete search history.

(56) References Cited

U.S. PATENT DOCUMENTS

| | | | |
|---|---|---|---|
| 4,663,358 A | 5/1987 | Hyon et al. | 521/64 |
| 5,705,780 A | 1/1998 | Bao | 204/157.15 |
| 5,981,826 A | 11/1999 | Ku et al. | 623/11 |
| 6,855,165 B2 | 2/2005 | Fell et al. | 623/14.12 |
| 6,855,743 B1* | 2/2005 | Gvozdic | 521/141 |
| 6,866,684 B2 | 3/2005 | Fell et al. | 623/20.3 |
| 6,911,044 B2 | 6/2005 | Fell et al. | 623/14.12 |
| 6,923,831 B2 | 8/2005 | Fell et al. | 623/14.12 |
| 7,282,165 B2* | 10/2007 | Williams et al. | 264/28 |
| 2004/0092653 A1 | 5/2004 | Ruberti et al. | |
| 2004/0133275 A1* | 7/2004 | Mansmann | 623/14.12 |
| 2004/0171740 A1 | 9/2004 | Ruberti et al. | |
| 2004/0220296 A1 | 11/2004 | Lowman et al. | |
| 2005/0049323 A1* | 3/2005 | Gvozdic | 521/141 |
| 2005/0287187 A1* | 12/2005 | Mansmann | 424/423 |

FOREIGN PATENT DOCUMENTS

WO    WO 2006/125082    11/2006

OTHER PUBLICATIONS

Bragdon et al., The Journal of Arthroplasty 16(5): 658-665 (2001).
Gong et al., Adv. Mater. 15(14): 1155-1158 (2003).
Kobayashi et al., Biomaterials 24: 639-647 (2003).
Tanaka et al., Prog. Polym. Sci. 30: 1-9 (2005).
Thomas et al., Journal of Biomedical Materials Research 69(2): 135-140 (2004) (XP-002352111).

* cited by examiner

*Primary Examiner* — Alexa Neckel
*Assistant Examiner* — Marie Reddick
(74) *Attorney, Agent, or Firm* — Quales & Brady, LLP

(57) ABSTRACT

The invention provides fabricated tough hydrogels, hydrogel-containing compositions, and methods of making the same. The invention also provides methods of implanting or administering the tough hydrogels, or the hydrogel-containing compositions to treat a subject in need. Methods of cross-linking pre-solidified or pre-gelled hydrogel particles and making crosslinked tough hydrogels, and crosslinked tough hydrogel-containing compositions also are disclosed herein.

14 Claims, 21 Drawing Sheets

(A)

(B)

TOUGH HYDROGELS

This application is a 371 of PCT/US2005/034662 filed Sep. 27, 2005, which claims priority to U.S. Provisional Application No. 60/687,317 filed Jun. 6, 2005, and U.S. Provisional Application No. 60/702,279 filed Jul. 26, 2005. The entire contents of the above-identified applications are hereby incorporated by reference.

FIELD OF THE INVENTION

The invention relates to fabrication of tough hydrogels, tough hydrogel-containing compositions, and methods of making fabricated tough hydrogels and tough hydrogel-containing compositions. The invention also relates to methods of using the fabricated tough hydrogels and tough hydrogel-containing compositions in treating a subject in need.

BACKGROUND OF THE INVENTION

Hydrogels are candidate biomaterials for device applications such as synthetic articular cartilage replacement in humans and animals. Hydrogels are polymeric structures that are hydrophilic and contain high concentrations of water. Typically hydrogels have the desirable properties of biocompatibility, low coefficient of friction, and high water content. However, most hydrogels lack the mechanical properties necessary to sustain the high loads that are present in most of the joints in the body. For instance, the axial load in the knee can go as high as three to five times the body weight of the patient. Under such loads, a hydrogel material replacing the function of the articular cartilage is expected to maintain its shape and function in the long-term. Some of the expected requirements from a hydrogel material to resist the mechanical cyclic loading and articulation of human joints are high stiffness, high strength, high toughness, high wear resistance, and/or low coefficient of friction against an opposing cartilage surface.

Most hydrogels systems available for articular cartilage replacement applications do not have required mechanical strength to withstand the high loads of the human joint. Various dehydration and deformation methods, described below, can be used together in combinations to improve the properties of hydrogels.

Solvent dehydration of hydrogels is described by Bao (U.S. Pat. No. 5,705,780). Bao describes immersion of PVA hydrogel into solvents such as ethanol/water mixture at room temperature to dehydrate PVA hydrogel without shape distortion.

Hyon and Ikada (U.S. Pat. No. 4,663,358) and Bao (U.S. Pat. No. 5,705,780) describe the use of water and organic solvent mixture to dissolve PVA powder and subsequently cooling the solution below room temperature and heating back up to room temperature to form a hydrogel. The hydrogel is then immersed in water to remove the organic solvent. Hyon and Ikada claim that PVA hydrogels thus formed are transparent as opposed to the ones formed by freeze-thaw method that uses water only as the solvent to dissolve the PVA powder.

Bao (U.S. Pat. No. 5,522,898) describes dehydration methods that use air dehydration, vacuum dehydration, or partial humidity dehydration to control the rate of dehydration and prevent shape distortion of PVA hydrogels for use as prosthetic spinal devices to replace the nucleus pulposus. The starting gels of Bao are the freeze-thaw gels described in the U.S. Pat. No. 5,705,780.

Ku et al. (U.S. Pat. No. 5,981,826) describes a freeze-thaw method to form a PVA hydrogel by subjecting a PVA aqueous solution to freeze thaw followed by immersion in water and additional cycles of freeze-thaw while immersed in water.

However, until the instant invention, the field lacked tough hydrogels for articular cartilage replacement applications that have required mechanical strength, and can withstand high loads of human joints.

SUMMARY OF THE INVENTION

The present invention relates generally to tough hydrogels, tough hydrogel-containing compositions, and methods of making tough hydrogels and tough hydrogel-containing compositions. The invention also relates to methods of using the tough hydrogels and tough hydrogel-containing compositions in treating a subject in need, for example, for articular cartilage replacement applications that meet required mechanical strength to withstand high loads of human joints.

One aspect of the invention provides methods of making a tough hydrogel comprising: contacting a hydrogel with an organic solvent, wherein the hydrogel comprises a polymer which is not soluble in the solvent, and wherein the solvent is at least partially miscible in water; heating the hydrogel to a temperature below or above the melting point of the hydrogel; and cooling the heated hydrogel to room temperature, wherein the method dehydrates the hydrogel, thereby forming a tough hydrogel.

Another aspect of the invention provides methods of making a tough hydrogel comprising: contacting a hydrogel with an organic solvent, wherein the hydrogel comprises a polymer which is not soluble in the solvent, and wherein the solvent is at least partially miscible in water; and air-drying the hydrogel at room temperature, wherein the method dehydrates the hydrogel, thereby forming a tough hydrogel.

Another aspect of the invention provides methods of making a tough hydrogel comprising: contacting a hydrogel with an organic solvent, wherein the hydrogel comprises a polymer which is not soluble in the solvent, and wherein the solvent is at least partially miscible in water; and subjecting the hydrogel to at least one freeze-thaw cycle and allowing the hydrogel to warm-up room temperature, wherein the method dehydrates the hydrogel sample, thereby forming a tough hydrogel.

Another aspect of the invention provides methods of dehydrating a hydrogel comprising: contacting a hydrogel with an organic solvent, wherein the hydrogel comprises a polymer which is not soluble in the solvent, and wherein the solvent is at least partially miscible in water; heating the hydrogel to a temperature below or above the melting point of the hydrogel; and cooling the heated hydrogel to room temperature.

Another aspect of the invention provides methods of dehydrating a hydrogel comprising: contacting a hydrogel with an organic solvent, wherein the hydrogel comprises a polymer which is not soluble in the solvent, and wherein the solvent is at least partially miscible in water; and air-drying the hydrogel at room temperature.

Another aspect of the invention provides methods of dehydrating a hydrogel comprising: contacting a hydrogel with an organic solvent, wherein the hydrogel comprises a polymer which is not soluble in the solvent, and wherein the solvent is at least partially miscible in water; and subjecting the hydrogel to at least one freeze-thaw cycle and allowing the hydrogel to warm-up room temperature.

Another aspect of the invention provides methods of making a tough hydrogel comprising the steps of: providing a polymeric material, wherein the polymeric material is PVA powder; mixing the polymeric material with water and/or PEG, thereby forming a solution; subjecting the solution to at least one freeze-thaw cycle, thereby forming a hydrogel; and dehydrating and/or deforming the hydrogel, thereby forming a tough hydrogel.

Another aspect of the invention provides methods of making a tough hydrogel comprising the steps of: providing a polymeric material, wherein the polymeric material is PVA powder; mixing the polymeric material with water and/or PEG at a temperature above the room temperature, thereby forming a solution; cooling the solution to an ambient temperature, thereby forming a hydrogel or hydrogel particles; and dehydrating and/or deforming the hydrogel, thereby forming a tough hydrogel.

According to another aspect, the invention provides methods as described above, wherein the hydrogel comprises PVA or hydrogel particles, wherein the hydrogel comprises water and/or one or more other ingredients. The ingredient is PVA, PEG, and/or salt, proteoglycan, water soluble polymer, amino acid, alcohol, DMSO, water soluble vitamin, wherein in the ingredients is partially or completely soluble in water.

According to another aspect, the ingredient is PEG, wherein the PEG is in a solution of water, ethanol, ethylene glycol, DMSO, or a suitable solvent.

According to another aspect, the ingredient is non-volatile.

According to another aspect, the ingredient is at least partially miscible in water.

According to another aspect, the ingredient is selected from the group consisting of PEG, salt, NaCl, KCl, CaCl, vitamins, carboxylic acids, hydrocarbons, esters, and amino acids, PEG of different molecular weights or a blend of PEGs of different molecular weights.

According to another aspect, the water miscible polymer is PEO, Pluronic, amino acids, proteoglycans, polyacrylamide, polyvinylpyrrolidone, polysaccharides, dermatin sulfate, keratin sulfate, or dextran sulfate.

According to another aspect, at least 0.1% of the hydrogel's weight constitutes one or more non-volatile ingredient.

According to another aspect, the dehydration is carried out by placing the hydrogel in: a) a non-solvent, wherein i. the non-solvent is PEG, isopropyl alcohol, saturated salinated water, vitamin, or carboxylic acid, aqueous solution of a salt of an alkali metal, and ii. the non-solvent contains more than one ingredient including water, PEG, vitamin, polymer, ester, proteoglycan, and carboxylic acid, or b) in a supercritical fluid.

According to another aspect, the dehydration is carried out by leaving the hydrogel in air, by placing the hydrogel in a vacuum at room temperature or at an elevated temperature, for example, at 40° C., above about 40° C., about 80° C., above 80° C., about 90° C., about 100° C., above 100° C., about 150° C., about 160° C., above 160° C., about 180° C., about 200° C., or above 200° C.

According to another aspect, the dehydration is carried out by heating the hydrogel in air or inert gas to elevated temperature, wherein the heating rate is slow or fast or the heating follows the vacuum or air dehydration.

According to another aspect, the dehydrated hydrogel is re-hydrated by placing the dehydrated hydrogel: i. in water, saline solution, Ringer's solution, salinated water, buffer solution, and the like, ii. in a humid chamber, or iii. at room temperature or at an elevated temperature.

According to another aspect, the above methods further comprise deforming the hydrogel.

According to another aspect, the above methods further comprise steps of heating to a temperature above about 40° C. to about 200° C. or more and deforming the hydrogel.

According to another aspect, the above methods further comprise steps of deforming and dePEGing a PEG-comprising hydrogel.

According to another aspect, the above method further comprise: a) heating to a temperature above about 40° C. to about 200° C. or more and deforming the hydrogel; and b) dePEGing a PEG-comprising hydrogel.

According to another aspect, the hydrogel is deformed by uniaxial compression, channel-die compression, or other modes of deformation.

According to another aspect, the hydrogels are heated to a temperature below the melting point of the hydrogel and deformed, wherein the hydrogel is deformed under compression using flat or curved platens, or one flat and one curved platen.

According to another aspect, the hydrogels are deformed under air or inert gas, or in fluid medium, wherein the fluid medium is a saline solution, Ringer's solution, PEG, aqueous PEG solution, salt solution, DMSO, or any suitable fluid medium.

According to another aspect, the hydrogels are deformed at a temperature that is below the melting point of the hydrogel, wherein the temperature is between about 0° C. and about 100° C., between about 10° C. and about 100° C., between about 0° C. and about 40° C., between about 10° C. and about 30° C., between about 17° C. and about 25° C., or at about room temperature.

According to another aspect, the hydrogels are dehydrated prior to or after deformation.

According to another aspect, the tough hydrogels made by above disclosed methods are re-hydrated to reach an equilibrium, wherein the tough hydrogels are re-hydrated in water or a salt solution.

In one aspect, the invention provides tough hydrogels comprising a polymer and water, wherein the tough hydrogels contain at least about 1% to about 50% equilibrium water content.

In another aspect, the invention provides tough hydrogels comprising dehydrated or deformed hydrogel made by a process according to any of the above claims.

In another aspect, the invention provides tough hydrogels made by any of the above described processes, wherein the tough hydrogel is capable of re-hydration following dehydration, wherein the dehydration reduces the weight of the hydrogel by more than 34%; and the re-hydration results in at least about 46% equilibrium water content in the re-hydrated hydrogel.

In another aspect, the tough hydrogels are of a biaxial orientation or of a uniaxial orientation, wherein the tough hydrogel has a high ultimate tensile strength.

Yet another aspect of the invention provides medical implants comprising a tough hydrogel, for example, an interpositional device, wherein the interpositional device a unispacer, wherein the unispacer is a free floating articular implant in human joints such as a knee, a hip, a shoulder, an elbow, or an upper or an extremity joint.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, and advantages of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

DETAILED DESCRIPTION OF THE INVENTION

This invention provides fabricated tough hydrogels, tough hydrogel-containing compositions, and methods of making tough hydrogels and tough hydrogel-containing compositions. The invention also provides methods of using the fabricated tough hydrogels and tough hydrogel-containing compositions in treating a subject in need.

Hydrogels described in the prior art (see for example, U.S. Pat. Nos. 4,663,358, 5,981,826, and 5,705,780, US Published Application Nos. 20040092653 and 20040171740) can be used as starting materials for making tough hydrogels of the present invention by employing methods described herein for the first time. The tough hydrogels provided in the present invention can be used in a body to augment or replace any tissue such as cartilage, muscle, breast tissue, nucleus pulposus of the intervertebral disc, other soft tissue, interpositional devices that generally serves as a cushion within a joint, etc.

Tough hydrogels generally include polymer, polymer blends, or copolymers of polyvinyl alcohol (PVA), polyvinyl pyrrolidone (PVP), poly ethylene oxide (PEO), polyacrylamide (PAAM), Polyacrylic acid (PAA), alginates, polysaccharides, polyoxyethylene-polyoxypropylene co-polymers, poly-N-alkylacrylamides, poly-N-isopropyl acrylamide (PNIAAm), chondroitin sulfate, dextran sulfate, dermatin sulfate, or combinations of two or more thereof.

Tough hydrogels, as disclosed herein, comprised of uniformly distributed hydrogel molecules or hydrogel particles comprising polyvinyl alcohol (PVA) copolymerized and/or blended with at least one of the other polymers or gellants, for example, polyvinyl pyrrolidone (PVP), poly-N-isopropyl acrylamide (PNIPAAm), poly ethylene oxide (PEO), chondroitin sulfate, dextran sulfate, dermatin sulfate and the like, or combinations of two or more thereof.

According to one aspect of the invention, the tough hydrogels comprise polyvinyl alcohol (PVA) copolymerized and/or blended with at least one of the other polymers.

According to another aspect of the invention, the hydrogel solutions comprise polyvinyl alcohol (PVA), polyvinyl pyrrolidone (PVP), poly ethylene oxide (PEO), poly-N-isopropyl acrylamide (PNIAAm), or combinations of two or more thereof.

According to another aspect of the invention, the hydrogel solution is a polyvinyl alcohol (PVA) solution.

Figure 1:
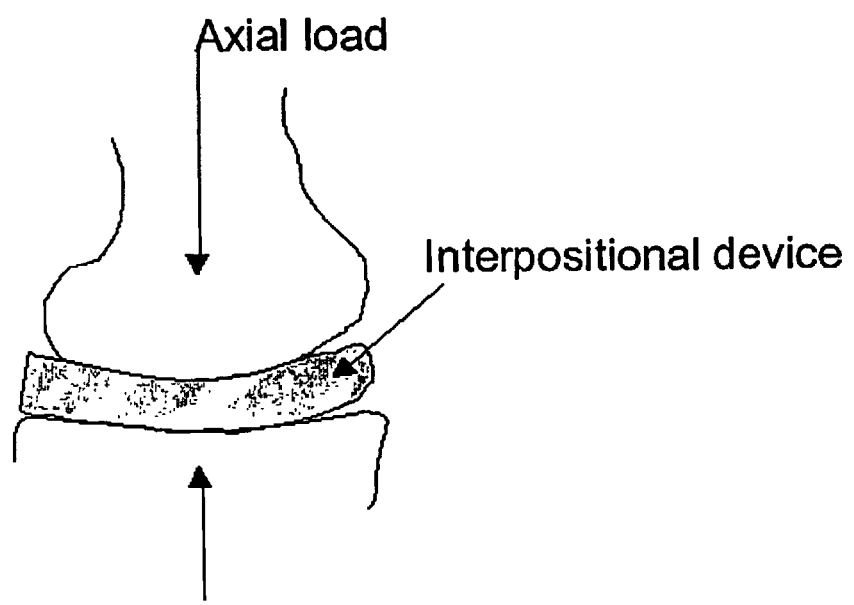
FIG. 1. A typical human joint showing an interpositional device loaded by the axial load applied by the human body.

Tough hydrogels of the invention can be used in a variety of fashions in joints in mammals such as human joints. For example, an interpositional device can be manufactured from the tough hydrogels, which meet required mechanical strength to withstand high loads of human joints, and can be used in articular cartilage replacement applications. The interpositional devices typically act as a cushion within the joint to minimize the contact of the cartilage surfaces to each other (see FIG. 1). This is beneficial in patients with arthritic joints. Early arthritic joints with cartilage lesions can be treated with such interpositional devices, which minimizes the contact between the damaged cartilage surfaces of the patient. The interpositional devices are described by Fell et al. (see U.S. Pat. Nos. 6,923,831, 6,911,044, 6,866,684, and 6,855,165). These devices can have a variety of shapes and sizes. For a hydrogel interpositional device to perform in vivo in the long-term, the device first needs to have a high creep resistance. This is to minimize the changes to the shape of the interpositional hydrogel device during in vivo use. Tough hydrogel materials of the invention with increased stiffness display increased creep resistance. The hydrogel interpositional device according to the invention also have superior mechanical properties, such as toughness, wear resistance, high creep resistance, etc.

Figure 2:
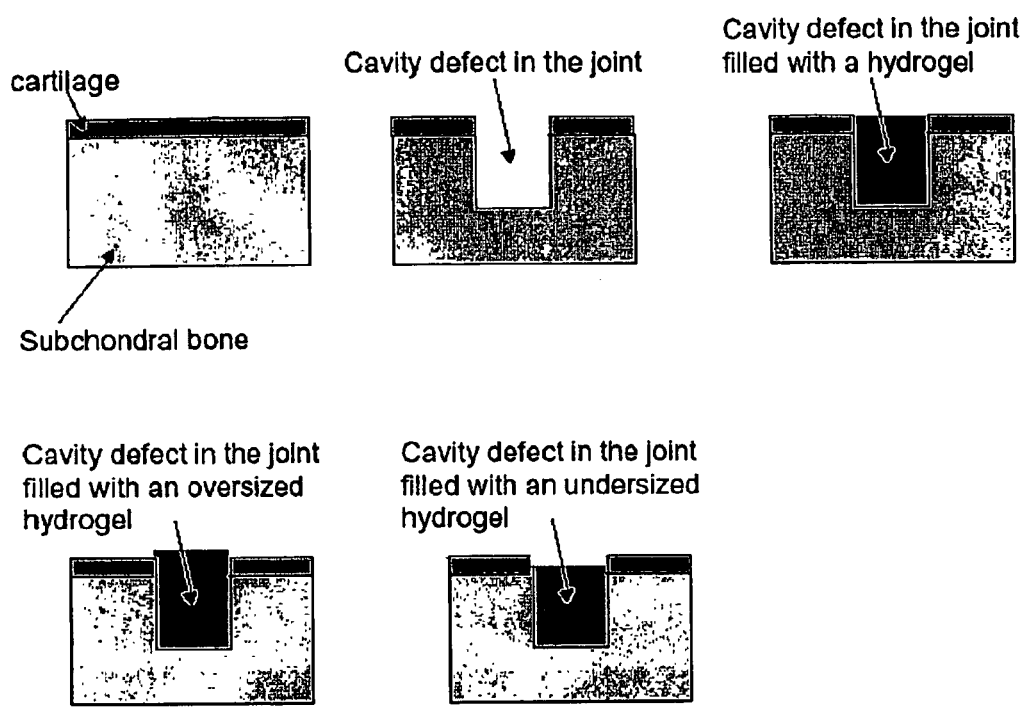
FIG. 2. Shows cavity defect in joints and filling with hydrogels.

Another method for the use of a hydrogel implant is through the filling of a cavity in the joint. The cavity can be an existing one or one that is prepared by a surgeon. A tough hydrogel plug can be inserted into the cavity. FIG. 2 shows an example of a cavity filled with a hydrogel plug. The hydrogel plug can be of any shape and size; for instance it can be cylindrical in shape. In some embodiments the plug can be oversized to be elevated from the surrounding cartilage surface. In other embodiments the plug can be undersized to stay recessed in the cavity. The over-sizing or under-sizing can be such that the plug can stand proud above the surrounding cartilage surface or recessed from the surrounding cartilage surface by about less than 1 mm, by about 1 mm, by more than about 1 mm, by about 2 mm, by about 3 mm, or by about more than 3 mm. In some embodiments the hydrogel plug can be slightly dehydrated to shrink its size and to allow an easy placement into the cavity. The hydrogel plug then can be hydrated and swollen in situ to cause a better fit into the cavity. The dehydrated and re-hydrated dimensions of the hydrogel plug can be tailored to obtain a good fit, under-sizing, or over-sizing of the plug after re-dehydration and re-swelling. The re-dehydration in situ can also be used to increase the friction fit between the plug and the cavity. This can be achieved by tailoring the dimensions and the extent of dehydration such that upon re-dehydration the cross-section of the plug can be larger than the cross-section of the cavity; by for instance about 1 mm, less than 1 mm, or more than 1 mm. In some embodiments the cavity is filled with an injectable hydrogel system that cures in situ such as the one described by Ruberti and Braithwaite (see US Published Application Nos. 20040092653 and 20040171740), Muratoglu et al (U.S. Provisional Application No. 60/682,0008, filed May 18, 2005), Lowman (US Published Application No. 2004/0220296), and other injectable systems.

The present invention provides methods of fabricating hydrogel systems to obtain tough hydrogels that can maintain shape under the high loads of human joints. According to one aspect of the invention, the tough hydrogels are obtained by improving the stiffness, toughness and strength of hydrogels to increase resistance to creep and resistance to wear. The invention provides dehydration methods to improve the mechanical properties of the hydrogel. The invention also provides permanent plastic deformation methods to increase the creep resistance of the hydrogel. Various dehydration and deformation methods, described above, can be used together in combinations to improve the properties of hydrogels. Any of the dehydration methods can be used either by itself or in combination with the other dehydration methods to improve the mechanical properties of hydrogels. Plastic deformation method also can be used by itself to increase the creep resistance of the hydrogels.

In the case of extreme dehydration of the hydrogel, it can be important for some of the applications to subsequently rehydrate the hydrogel at least to some extent to regain the lubrication imparted by the presence of water for some of the embodiments. If the heat dehydration is carried out starting with a hydrogel that contains water and one or more other ingredient(s), which are in most embodiments non volatile such as low molecular weight PEG, and others such as PVP, PEO, chondrotin sulfate, the dehydrated hydrogel is easily re-hydrated to varying levels. According to one aspect of the invention, the level of re-hydration following heat dehydration depends on the concentration of other ingredient(s) in the water phase of the initial hydrogel before dehydration. In contrast, if the starting hydrogel contains no other ingredients but water, then the extent of re-hydration subsequent to heat dehydration is substantially reduced compared to the re-hydration levels of the hydrogels dehydrated in the presence other ingredient(s). The presence of the other ingredient(s) other than water also has implication on the creep behavior of the hydrogel following heat dehydration and subsequent re-hydration. The hydrogel is more viscoelastic when it is heat treated in the presence of other ingredient(s).

According to another aspect, PVA hydrogels containing a low molecular weight ingredient, such as PEG, retain their opacity during heat dehydration. In contrast, PVA hydrogels containing no such ingredients and heat dehydrated under identical conditions lose their opacity and turn transparent, an indication for the loss of the molecular porosity. The molecular porosity is thought to be the free space in the structure where the water molecules penetrate the hydrogel, thus hydrating it. The loss of the opacity upon heat dehydration of hydrogels not containing any such ingredient can be the reason for their substantially reduced ability to re-hydrate. According to one aspect on the invention, the non-volatile ingredient remains in the hydrogel structure during heat dehydration and prevents the collapse of the molecular porosity, and thus allowing these hydrogels to re-hydrate following heat dehydration.

The invention also provides freeze-thaw prepared PVA (FT-PVA) hydrogels, wherein the hydrogel is toughened by annealing at around 160° C. Upon re-hydration, the annealed gels remain transparent forming an elastic and tough, almost rubber-like material. While this material is useful in some application, it may not be for applications requiring high water content in the hydrogel. The extent of re-hydration is further tailored in the annealed FT-PVA by adding an ingredient such as PEG into the water phase prior to the annealing.

The invention also provides in another aspect that the permanent deformation can be used to substantially increase the creep resistance of hydrogels. In addition, high dose irradiation also can increase the cross-link density of the hydrogels.

In one embodiment, the hydrogel material is plastically deformed. The plastic deformation introduces molecular orientation into the material. The material increases creep resistance in the direction in which it is deformed. Therefore, it can be used as a high creep resistant implant. In one embodiment the implant is fabricated such that the deformation is in the direction of the axial load applied in the human joint, see FIG. 1, for example.

In another embodiment, the plastic deformation is induced by uniaxial compression, channel-die compression tension, bending, shear, or other modes of deformation. The plastic deformation is induced at any temperature below the melting point of the hydrogel. The plastic deformation is induced statically or dynamically. In another embodiment, the deformation is induced by uniaxial compression. In another embodiment the deformation is induced by channel-die deformation. See FIG. 3 for examples of deformation types.

In another embodiment, the hydrogels are deformed under compression using flat or curved platens. The flat platens result in flat deformed surfaces of the hydrogel. The curved platens result with curved deformed surfaces (see FIG. 3). In another embodiment the deformation is induced by one flat and one curved platen.

In another embodiment, the deformation of the hydrogel is carried out with shaped platens such that the deformed hydrogel become the final implant shape or the near-net shape of the final implant.

In another embodiment, the deformed hydrogel is machined further to obtain the final implant shape.

In another embodiment, the hydrogel implant is packaged and sterilized. The packaging can be such that the hydrogel device is immersed in an aqueous solution to prevent dehydration until implantation, such as during sterilization and shelf storage. The aqueous solution can be water, deionized water, saline solution, Ringer's solution, or salinated water. The aqueous solution also can be a solution of poly-ethylene glycol in water. The solution can be of less than 5% (wt) in PEG, about 5% (wt), more than about 5% (wt), about 10% (wt), about 15% (wt), about 20% (wt), about 30% (wt), about 50% (wt), about 90% (wt) or about 100% (wt). The hydrogel device also can be sterilized and stored in a non-volatile solvent or non-solvent.

The sterilization of the hydrogel implant is carried out through gamma sterilization, gas plasma sterilization, or ethylene oxide sterilization. According to one embodiment, the hydrogel is sterilized by autoclave. The sterilization is carried out at the factory; or alternatively, the implant is shipped to the hospital where it is sterilized by autoclave. Some hospitals are fitted with ethylene oxide sterilization units, which also is used to sterilize the hydrogel implant.

In one embodiment, the hydrogel implant is sterilized after packaging. In other embodiments the hydrogel implant is sterilized and placed in a sterile aqueous solution.

In another embodiment, PVA hydrogel is prepared using the freeze-thaw method starting with an aqueous PVA solution (at least about 1% (wt) PVA, above about 1% (wt) PVA, about 5% (wt) PVA, about 10% (wt) PVA, above about 10% (wt) PVA, about 15% (wt) PVA, about 20% (wt) PVA, about 25% (wt) PVA, about above 25% (wt) PVA) and subjecting it to freeze-thaw cycles (at least 1 cycle, more than 1, 2, 3, 4, 5, 6, 7, 8, 9, 10 or more cycles). The freeze-thaw cycle is defined as cooling the PVA solution below 0° C. and heating it back up above 0° C. The PVA hydrogel is then subjected to dehydration. Subsequently, the dehydrated hydrogel is placed in saline solution for re-hydration. This process results in very little re-hydrated PVA hydrogel with high mechanical strength.

In one embodiment of the invention, PEG is used as a non-volatile non-solvent for PVA hydrogels. DMSO is used instead of water in preparing the aqueous PVA solution, the precursor to the hydrogel.

In one embodiment of the invention, PEG solution is a solution of PEG in a solvent (preferably water, ethanol, ethylene glycol, DMSO, or others). The solution concentration can be anywhere between 0.1% (wt) PEG and 99.9% (wt) PEG. The PEG in the solution can be of different molecular weights (preferably 300, 400, or 500 g/mol, more than 300 g/mol, 1000 g/mol, 5000 g/mol or higher). The PEG in the solution can be a blend of different average molecular weight PEGs.

In another embodiment, PEG containing PVA hydrogel is prepared using the freeze-thaw method starting with an aqueous PVA solution (at least about 1% (wt) PVA, above about 1% (wt) PVA, about 5% (wt) PVA, about 10% (wt) PVA, above about 10% (wt) PVA, about 15% (wt) PVA, about 20% (wt) PVA, about 25% (wt) PVA, about above 25% (wt) PVA) and subjecting it to freeze-thaw cycles (at least 1 cycle, more than 1, 2, 3, 4, 5, 6, 7, 8, 9, 10 or more cycles). At this step the PVA hydrogel can be optionally placed in saline to reach full hydration. Subsequently, the gel is placed in a low molecular weight PEG solution. This is to dope the hydrogel with the non-solvent PEG. The duration of PEG solution soak can be varied to either reach a uniform equilibrium PEG content throughout the hydrogel or to reach a non-uniform PEG distribution (by shortening the soak duration). The latter results in PEG-rich skin and a gradient of PEG concentration within the PVA hydrogel.

In another embodiment, PEG containing PVA hydrogel is prepared by starting with an aqueous PVA solution (at least about 1% (wt) PVA, above about 1% (wt) PVA, about 5% (wt) PVA, about 10% (wt) PVA, above about 10% (wt) PVA, about 15% (wt) PVA, about 20% (wt) PVA, about 25% (wt) PVA, about above 25% (wt) PVA) and mixing it with a low molecular weight PEG solution at an elevated temperature (above room temperature or above 50° C.). Upon cooling down to room temperature, the mixture forms a PVA hydrogel containing water and the non-solvent PEG. In another embodiment, the hot PVA/PEG mixture is not cooled to room temperature but instead is subjected to freeze-thaw cycles.

In another embodiment, PVA hydrogel is heat dehydrated. The PVA hydrogel contains PEG during heat dehydration (or annealing). The heat dehydration is carried out at 40° C., at above about 40° C., at 80° C., at above 80° C., at 90° C., at 100° C., at above 100° C., at 150° C., at 160° C., at above 160° C., at 180° C., at 200° C., or at above 200° C. The heat dehydration can be carried out in any environment, preferably in an inert gas like nitrogen or argon or in vacuum. The heat dehydration also can be carried out in air or acetylene gas or mixture of a number of gases. The heat dehydration can be carried out either by placing the hydrogel in an already heated environment to achieve a higher rate of heat dehydration or by heating the hydrogel slowly to achieve a slower rate of heat dehydration. The rate of heat dehydration can be such that the hydrogel loses weight from removal of water at a rate of 1% weight loss per day, 10% weight loss per day, 50% weight loss per day, 1% weight loss per hour, 10% weight loss per hour, 50% weight loss per hour, 1% weight loss per minute, 5% weight loss per minute, 10% weight loss per minute, 50% weight loss per minute or any amount thereabout or therebetween. The rate of heat dehydration depends on the rate at which the temperature is raised and the size of the hydrogel. Prior to heat dehydration, the hydration level of the hydrogel can be reduced by vacuum dehydration. Subsequent to the heat dehydration the hydrogel is placed in saline solution for re-hydration. This results in good levels of re-hydration in the PVA hydrogel resulting in high mechanical strength and good lubrication when articulating against human cartilage or other hydrophilic surfaces. This hydrogel is expected to maintain its hydrogen bonded structure, thus is not be subject to dissolution over long-term in water, saline or bodily fluid.

Although the description and examples are given for a PVA hydrogel systems, but can be applied to any hydrogel system of a polymeric structure, that is, with long-chain molecules. Therefore, the invention provides hydrogel systems that includes, but not limited to, PVA as the base material.

Polymeric materials can be oriented by mechanical deformation. The deformation results in molecular orientation. Typically, the mechanical properties in the direction of the molecular orientation is superior to those of the isotropic, undeformed polymeric structure. The invention utilized this property of polymeric materials to improve the mechanical properties of hydrogel systems. By imposing a molecular orientation on a hydrogel material, the stiffness as well as the strength of the polymeric material is improved.

At any step of fabrication, the hydrogel can be irradiated by e-beam or gamma to cross-link. The irradiation can be carried out in air, in inert gas, in sensitizing gas, or in a fluid medium such as water, saline solution, polyethylene-glycol solution, etc. The radiation dose level is between one kGy and 10,000 kGy, preferably 25 kGy, 40 kGy, 50 kGy, 200 kGy, 250 kGy, or above.

The term "hydrogel" refers to undeformed or deformed hydrogel or tough hydrogels. The term "hydrogel", as described herein, also encompasses "tough hydrogels" including de-hydrated and/or deformed hydrogels. Tough hydrogels are networks of hydrophilic polymers containing absorbed water that can absorb a large amounts of energy, such as mechanical energy, before failure.

According to one aspect of the invention, polyvinyl alcohol (PVA) can be used as the base hydrogel. The base PVA hydrogel can be prepared by the well-known freeze-thaw method by subjecting a PVA solution (PVA can be dissolved in solvents such as water or DMSO) to one or multiple cycles of freeze-thaw. PVA solution used in the freeze-thaw method can contain another ingredient like PEG. The base PVA hydrogel also can be prepared by radiation crosslinking of a PVA solution. Another method of preparing the PVA hydrogel can be used to blend a PVA solution with a gellant such as (PEG) at an elevated temperature and cooling down to room temperature.

In one embodiment, the hydrogel can be of any shape, such a cubical shape, cylindrical shape, rectangular prism shape, or implant shape.

In another embodiment, NIPAAM can be used as the base hydrogel. The base NIPAAM hydrogel can be prepared by radiation crosslinking of a NIPAAM solution. Alternatively, the methods described by Lowman et al. can be used.

In another embodiment, a double network (DN) hydrogel structure can be used as the base hydrogel. The base DN hydrogel can be prepared by methods described by Gong et al. (see *Advanced Materials*, 2003, 15, No. 14: 1155-1158). The first network can be formed by reacting hydrophilic monomers such as 2-acrylamindo-2-methylpropanesulfonic acid (AMPS) in presence of cross-linking agents. The gel is then immersed in the aqueous solution containing another type of monomer such as acrylic amide (AAm). Subsequent synthesis of the second network from those newly introduced monomers produces the DN hydrogel can be used as the base hydrogel.

In another embodiment, a topological gel (TP) can be used as the base hydrogel. The base TP hydrogel can be prepared by methods described by Tanaka et al. (see *Progress in Polymer Science*, 2005, 30:1-9). The polymer chains in TP gels are flexibly bound by cross-linkers that are sliding along the individual chain.

In the following embodiments, a nanocomposite (NC) gel structure can be used as the base hydrogel. The base NC hydrogel can be prepared by methods described by Tanaka et al. (see *Prog. Polym. Sci.* 2005, 30:1-9).

In some of the embodiments a dehydrated hydrogel can be used as the base hydrogel. The level of dehydration can be controlled such that the base hydrogel contains between 99% and 1% water, more preferably between 99% and 5% water, more preferably between 99% and 25% water, more preferably between 99% and 50% water, more preferably between 99% and 75% hydrogel, more preferably about 70% (wt) water, or 80% (wt) water.

The water content of the hydrogel can be determined by measuring the weight change of between its equilibrium hydration level and its dehydrated level.

In some embodiments, a hot solution of PVA/PEG in water is cooled down to room temperature and is used in its "as-gelled" form.

According to one aspect of the invention, the PVA/PEG hydrogel is immersed in water, deionized water, saline solution, phosphate buffered saline solution, Ringer's solution or salinated water to remove the PEG. The process is called the dePEGing process. During dePEGing the hydrogel also absorbs water approaching equilibrium water content. Therefore, dePEGing also is a re-hydration process.

In one of the embodiments, the hydrogel is deformed under load to create a permanent deformation.

In another embodiment, the hydrogel or the deformed hydrogel is dehydrated.

In another embodiment, the dehydrated hydrogel is re-hydrated. In some of the embodiments, the re-hydrated hydrogel contains less water than the hydrogel did before the dehydration step.

In some embodiments, the hydrogel dimensions are large enough so as to allow the machining of a medical device.

In some embodiments the starting hydrogel is dehydrated before any deformation.

In some embodiments the hydrogel is subjected to sequential dehydration and deformation cycles.

In some embodiments the hydrogel is subjected to simultaneous dehydration and deformation cycles.

Dehydration of the hydrogel can be achieved by a variety of methods. For instance, the hydrogel can be placed in vacuum at room temperature or at elevated temperatures to drive out the water and cause dehydration. The amount of vacuum can be reduced by adding air or inert gas to the vacuum chamber where the hydrogel is placed during dehydration. Dehydration of the hydrogel also can be achieved by keeping it in air or inert gas at room temperature or at an elevated temperature. Dehydration in air or inert gas also can be carried out at temperatures lower than room temperature. In most embodiments, if the dehydration is carried out at elevated temperatures, it is necessary to keep the temperature below the melting point of the hydrogel. However, the melting point of the hydrogel can increase during the dehydration step and make it possible to go to higher temperatures as the dehydration evolves. Dehydration of the hydrogel also can be carried out by placing the hydrogel in a solvent. In this case the solvent drives the water out of the hydrogel. For example, placing of PVA hydrogel in a low molecular weight PEG (higher than 100 g/mol, about 300-400 g/mol, about 500 g/mol) can cause dehydration of the PVA hydrogel. In this case the PEG can be used as pure or in a solution. The higher the PEG concentration the higher the extent of dehydration. The solvent dehydration also can be carried out at elevated temperatures. These dehydration methods can be used in combination with each other.

Re-hydration of the hydrogel can be done in water containing solutions such as, saline, water, deionized water, salinated water, or an aqueous solution or DMSO.

In some embodiments, the hydrogel is shaped into a medical device and subsequently dehydrated. The dehydrated implant is then re-hydrated. The initial size and shape of the medical implant is tailored such that the shrinkage caused by the dehydration and the swelling caused by the subsequent re-hydration (in most embodiments the dehydration shrinkage is larger than the re-hydration swelling) result in the desired implant size and shape that can be used in a human joint.

In some of the embodiments the starting shape of the hydrogel before deformation can be a rectangular prism, a cylinder, a cube, or a non-uniform shape.

In one embodiment, the hydrogel is uniaxially compressed between two metal plates. The deformed hydrogel is then held under constant deformation for an extended period of time to achieve permanent deformation. The extent of deformation is measured in terms of compression ratio which equals the ratio of the initial height of the sample to the final height of the sample. The extent of deformation is also measured in terms of strain, which equals the ratio of the displacement to the initial height of the samples. The preferred extent of deformation measured by strain is between 10% and 99%, more preferably 20% and 95%, more preferably 50% and 95%, more preferably 75% and 95%, more preferably 80% and 90%, and most preferably 90% or any value thereabout or therebetween. After holding the constant deformation the deformed hydrogel is removed form the press. In some embodiments the deformation is held for a sufficient amount of time to allow stress relaxation to reach equilibrium. In some other embodiments the hydrogel is subjected to cyclic loading during deformation.

Figure 3:
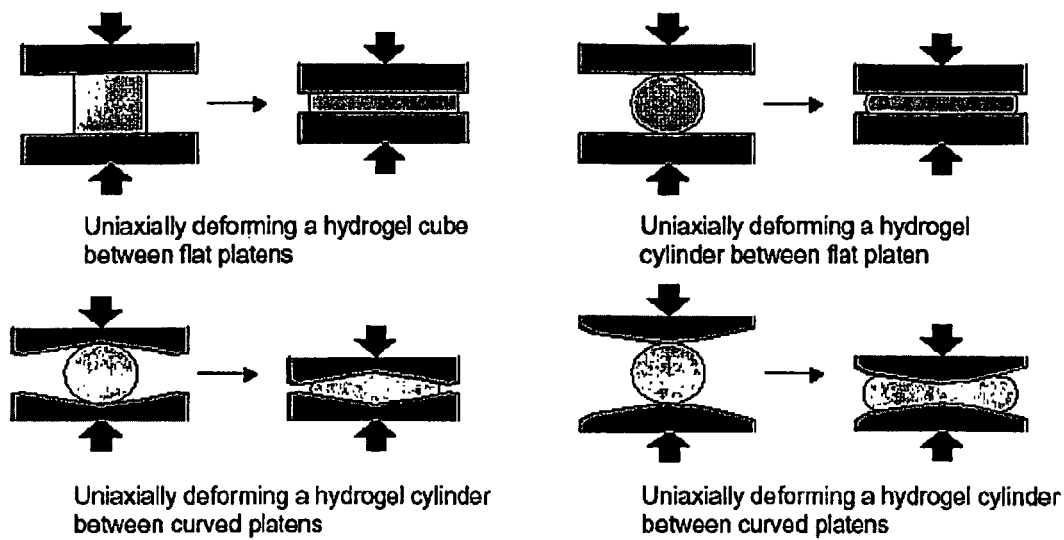
FIG. 3. Shows uniaxial deformation of hydrogels.

In one of the embodiments, the deformation induced in the hydrogel is achieved by placing the hydrogel in a channel-die, then compressing it in the channel-die to achieve orientation of the molecules primarily in the flow direction as shown in FIG. 3. The preferred extent of deformation ratio is between 10% and 99%, more preferably 20% and 95%, more preferably 50% and 95%, more preferably 75% and 95%, more preferably 80% and 90%, and most preferably 90% or any value thereabout or therebetween.

In another embodiment, the deformation of the hydrogel is achieved by placing the hydrogel in a channel-die, whereby the width of the block is smaller than the width of the channel-die. During initial stages of the deformation there can be biaxial orientation of the molecules until the hydrogel block makes contact with the walls of the channel-die, after which point the continued molecular orientation can take place primarily in one direction, which is the flow direction within the channel-die. In these embodiments the deformed hydrogel can have different levels of deformation in the two orthogonal directions (principal directions of deformation) within the plane of deformation. The direction of compression is normal to the plane of deformation.

In another embodiment, the deformation of the block is achieved under uniaxial tension.

In certain embodiments the deformation is carried out at a deformation rate lower than about 1 mm/min, at about 1 mm/min, more preferably between 1 mm/min and 10 m/min, more preferably between 10 mm/min and 100 mm/min, more preferably at about 20 mm/min or any value thereabout or therebetween.

In some embodiments the deformation is applied cyclically.

In some of the embodiments the deformation is applied sequentially. In these embodiments the hydrogel is deformed to a portion of the desired deformation ratio, held under constant deformation to allow some stress relaxation, and the deformation and stress relaxation steps are repeated until the desired deformation ratio is achieved. For instance, if the ultimate desired deformation ratio corresponds to a strain of 90%, the hydrogel can be deformed in 30% increments with a stress relaxation between each increment.

In certain embodiments, the deformation is carried out in gas medium such as air or inert gas, or in fluid medium such as saline, DMSO, or PEG. In some embodiments the medium is heated during the deformation to below the melting point of the deforming hydrogel. The melting point of the hydrogel may change during deformation; therefore, the temperature of the medium is adjusted to avoid melting.

In some embodiments the deformation is carried out in a fluid medium such as saline solution, Ringer's solution, PEG, aqueous PEG solution, salt solution and other fluid medium.

In certain embodiments the deformation is carried out at room temperature between about 10° C. and about 30° C., more preferably between about 17° C. and about 25° C., more preferably below the melting point of the hydrogel, more preferably between about 0° C. and about 40° C., more preferably between about 10° C. and about 100° C. or any temperature thereabout or therebetween.

In one of the embodiments, the hydrogel is compressed in a uniaxial compression mode between two platens, where the surfaces of the platens abutting the hydrogel during deformation are shaped so that the final compressed hydrogel has the desired final shape of the interpositional device.

In one of the embodiments, the hydrogel is compressed in a channel-die, where the plunger and the die surfaces abutting the hydrogel during deformation are shaped so that the final compressed hydrogel has the desired final shape of the interpositional device.

In certain embodiments, the hydrogel or deformed hydrogel can be machined into a desired shape to act as medical device, such as a kidney shaped interpositional device for the knee, a cup shaped interpositional device for the hip, a glenoid shaped interpositional device for the shoulder, other shapes for interpositional devices for any human joint. Also the machining of the hydrogel or deformed hydrogel can result in a cylindrical, cuboid, or other shapes to fill cartilage defects either present in the joint or prepared by the surgeon during the operation.

The hydrogel medical device can be an interpositional device such as a unispacer, to act as a free floating articular implant in a human joint, such as the knee joint, the hip joint, the shoulder joint, the elbow joint, and the upper and lower extremity joints.

In some of the embodiments, following the deformation, the deformed hydrogel is dehydrated. Subsequently the dehydrated gel is placed in saline solution for re-hydration.

In some of the embodiments where the hydrogel is sequentially deformed, the deformed hydrogel can be dehydrated to different levels at all or some of the steps of the sequential deformation before the subsequent step of deformation.

In some of the embodiments, the hydrogel or the deformed hydrogel is placed in 100% PEG to dehydrate the deformed hydrogel. Subsequently the dehydrated gel is placed in saline solution for re-hydration. This process decreases the equilibrium water content in the gel, and hence result in further improves the mechanical properties hydrogel.

In other embodiments, the hydrogel or deformed hydrogel is placed in a PEG-water solution for controlled dehydration followed by re-hydration in saline. The concentration of the PEG-water solution can be tailored to achieve desired level of dehydration of the hydrogel. Higher dehydrations provide more improvements in mechanical properties and at lower dehydrations the improvement is less. In some applications, it is desirable to achieve a lower stiffness; therefore a lower PEG and/or water concentration solution can be used for the dehydration process.

In some embodiments the hydrogel or the deformed hydrogel is dehydrated in vacuum at room temperature or at an elevated temperature. The vacuum dehydration can be carried out at about 10° C., above about 10° C., about 20° C., about 30, 40, 50, 60, 75, 80, 90° C., about 100° C. or above 100° C., or at 130° C. or any temperature thereabout or therebetween.

In some embodiments the vacuum dehydration of the hydrogel or the deformed hydrogel is first carried out at room temperature until a desired level of dehydration is reached; thereafter the temperature is increased to further dehydrate the hydrogel. The temperature is increased, preferably to above about 100° C., to about 160° C., or to above 160° C.

In some embodiments, the hydrogel is heated in air or inert gas or partial vacuum of inert gas for dehydration.

In some of these embodiments, the hydrogel is vacuum dehydrated before heating in air or inert gas.

In some embodiments, the heating of the hydrogel is carried out slowly; for example at less than about 1° C./min, at more than about 1° C./min, at 2, 5, 10° C./min or faster. Slower heating rates results in stronger gels than higher heating rates with some of the hydrogel formulations.

In most embodiments the finished medical device is packaged and sterilized.

In some of the embodiments the hydrogel is subjected to dehydration steps. The dehydration is carried out in air or in vacuum or at an elevated temperature (for instance annealing at about 160° C.). The dehydration causes loss of water hence a reduction in volume accompanied by a reduction in weight. The weight loss is due to loss of water. The reduction in volume on the other hand could be due to the loss of water or further crystallization of the hydrogel. In some embodiments the dehydration is carried out by placing the hydrogel in a low molecular weight polymer (for instance placing a PVA hydrogel in a PEG solution). In some cases the dehydration is caused by loss of water, but in most cases, there is also uptake of the non-solvent by the hydrogel. Therefore, the weight change of the hydrogel is the sum of loss of water and uptake of the non-solvent. The change in volume in this case is due to loss of water, uptake of the non-solvent, further crystallization of the hydrogel, or partial collapse of the porous structure of the non-solvent that is not occupying the space that water was filling in the pores.

In some of the embodiments, the hydrogel is attached to a metal substrate. The metal substrate is a porous backside surface that is used for bone-in-growth in the body to fix the hydrogel implant in place. The metal substrate attachment to the hydrogel can be achieved by having a porous surface on the substrate where it makes contact with the hydrogel; the porous surface can be infiltrated by the gelling hydrogel solution (for instance a hot PVA and/or PEG mixture in water); when the solution forms a hydrogel, the hydrogel can be interconnected with the metal substrate by filling the porous space.

In some embodiments, there can be more than one metal substrate attached to the hydrogel for fixation with the hydrogel in the body to multiple locations.

In some embodiments, the hydrogel/metal substrate construct can be used during the processing steps described above, such as dePEGing, solvent dehydration, non-solvent dehydration, irradiation, packaging, sterilization etc.

In some of the embodiments the hydrogel contains hyaluronic acid (HA), either by having HA present in the solutions used to make the hydrogel and/or by diffusing HA into the hydrogel. In some of the embodiments the HA-containing hydrogel is irradiated. The irradiation can be carried out before, after, or during the processing steps such as vacuum dehydration, non-solvent dehydration, re-hydration, annealing, and/or deformation. The irradiation cross-links the hydrogel matrix and in some embodiments also forms covalent bonds with the HA. Addition HA to some of the hydrogels increases the lubricity of the hydrogel implant. This is beneficial for the tough hydrogels contain substantially reduced water content.

In some of the embodiments the hydrated hydrogel implants are slightly heated at the surface to partially melt the hydrogel and allow it to reform with more uptake and more lubricity.

In some of the embodiments a microwave oven is used to prepare the PVA solution. The PVA powder is place in water and the mixture is heated in a microwave oven to form a solution.

In some of the embodiments the heat dehydration or annealing of the hydrogel is performed in a microwave oven.

According to one embodiment of the invention, tough gel is prepared by a process comprising the steps of: providing polymeric material such as PVA powder; mixing with water at temperature above the room temperature (such as at about 50° C.-60° C.), thereby forming a solution; subjecting the solution to at least one freeze-thaw cycle or heating to a temperature below the melting temperature such as about 80° C.; cooling the heated solution to an ambient temperature such as room temperature, thereby forming a hydrogel (which is generally uniform, may also contain hydrogel particles); and deforming and/or dehydrating the hydrogel, thereby forming the tough hydrogel. In another embodiment, optionally the hydrogel is dehydrated by heating from about 40° C. to above 200° C. and is subject to dePEGing.

One embodiment of the invention provides methods of making a tough hydrogel comprising: a) contacting a hydrogel with an organic solvent, wherein the hydrogel comprises a polymer which is not soluble in the solvent, and wherein the solvent is at least partially miscible in water; b) heating the hydrogel to a temperature below or above the melting point of the hydrogel; and c) cooling the heated hydrogel to room temperature, wherein the method dehydrates the hydrogel, thereby forming a tough hydrogel.

Another embodiment of the invention provides methods of making a tough hydrogel comprising: a) contacting a hydrogel with an organic solvent, wherein the hydrogel comprises a polymer which is not soluble in the solvent, and wherein the solvent is at least partially miscible in water; and b) air-drying the hydrogel at room temperature, wherein the method dehydrates the hydrogel, thereby forming a tough hydrogel.

Another embodiment of the invention provides methods of making a tough hydrogel comprising: a) contacting a hydrogel with an organic solvent, wherein the hydrogel comprises a polymer which is not soluble in the solvent, and wherein the solvent is at least partially miscible in water; and b) subjecting the hydrogel to at least one freeze-thaw cycle and allowing the hydrogel to warm-up room temperature, wherein the method dehydrates the hydrogel sample, thereby forming a tough hydrogel.

Another embodiment of the invention provides methods of making a tough hydrogel comprising the steps of: a) providing a polymeric material, wherein the polymeric material is PVA powder; b) mixing the polymeric material with water and/or PEG, thereby forming a solution; c) subjecting the solution to at least one freeze-thaw cycle, thereby forming a hydrogel; and d) dehydrating and/or deforming the hydrogel, thereby forming a tough hydrogel.

Another embodiment of the invention provides methods of making a tough hydrogel comprising the steps of: a) providing a polymeric material, wherein the polymeric material is PVA powder; b) mixing the polymeric material with water and/or PEG at a temperature above the room temperature, thereby forming a solution; c) cooling the solution to an ambient temperature, thereby forming a hydrogel or hydrogel particles; and d) dehydrating and/or deforming the hydrogel, thereby forming a tough hydrogel.

Embodiments and aspects of the invention also include:

1. Hydrogels that are capable of re-hydration following dehydration, wherein the tough hydrogel is capable of re-hydration following dehydration, wherein a) the dehydration reduces the weight of the hydrogel by more than about 34%; and b) the re-hydration results in at least about 46% equilibrium water content in the re-hydrated hydrogel.
2. Hydrogels with biaxial orientation.
3. Hydrogels with uniaxial orientation (by channel die deformation).
4. Hydrogels with a high ultimate tensile strength.
5. Methods for deforming hydrogels, wherein
   a. the hydrogel contains water and/or one or more other ingredient (for example, PEG, proteoglycans, water soluble polymers, salts, amino acids, alcohols, DMSO, water soluble vitamins), where the additional ingredients can be completely or partially soluble in water;
   b. the ingredient is non-volatile;
   c. the ingredient is at least partially miscible with water;
   d. at least 0.1% of the hydrogel's weight constitutes one or more non-volatile ingredient, such as PEG, and the like;
   e. the ingredient is a water miscible polymer such as PEO, Pluronic, amino acids, proteoglycans, polyacrylamide, polyvinylpyrrolidone, and the like;
   f. the ingredient is selected from the group of PEG, salt, NaCl, KCl, CaCl, vitamins, carboxylic acids, hydrocarbons, esters, amino acids and the like;
   g. the ingredient is PEG, wherein
      i. PEG of different molecular weights, or
      ii. blends of PEGs;
   h. the hydrogel is dehydrated prior to or after deformation, for example,
      i. dehydration by placing in a non-solvent, which is completely or partially water miscible, wherein
         a. the non-solvent is selected from PEG, isopropyl alcohol, saturated salinated water, vitamins, and carboxylic acids,
         b. the non-solvent contains more than one ingredient such as water, PEG, vitamins, polymers, esters, proteoglycans, and the like, and
         c. melting the hydrogel, which is a mixture.
      ii. dehydration by leaving the hydrogel in air,
      iii. dehydration by placing the hydrogel in vacuum,
      iv. dehydration by placing the hydrogel in vacuum at room temperature,
      v. dehydration by placing the hydrogel in vacuum at an elevated temperature, or
      vi. dehydration by placing in a supercritical $CO_2$.
   i. the deformation is uniaxial; or
   j. the deformation is carried out by channel-die.
6. Dehydration of a hydrogel containing water and/or one or more other ingredient (for example, PEG or Salt), wherein
   a. the ingredient is non-volatile such as PEG;
   b. the ingredient is at least partially miscible with water;
   c. at least 0.1% of the hydrogel's weight constitutes one or more non-volatile ingredient, such as PEG, hydrocarbons, and the like;
   d. the ingredient is a water miscible polymer such as PEO, Pluronic, amino acids, proteoglycans, polyvinylpyrrolidone, polyacrylamide, polysaccharides, dermatin sulfate, keratin sulfate, dextran sulfate, and the like;
   e. the ingredient is selected from the group of PEG, salt, NaCl, KCl, CaCl, vitamins, carboxylic acids, hydrocarbons, esters, amino acids, and the like;
   f. the ingredient is PEG, wherein
      i. PEG of different molecular weights, or
      ii. blends of PEGs,
   g. the dehydration is carried out by placing in a non-solvent, wherein
      i. the non-solvent is selected from PEG, isopropyl alcohol, saturated salinated water, aqueous solution of a salt of an alkali metal, vitamins, carboxylic acids, and the like, or
      ii. the non-solvent contains more than one ingredient such as water, PEG, vitamins, polymers, proteoglycans, carboxylic acids, esters, and the like.
   h. the dehydration is carried out by leaving the hydrogel in air;
   i. the dehydration is carried out by placing the hydrogel in vacuum;
   j. the dehydration is carried out by placing the hydrogel in vacuum at room temperature;
   k. the dehydration is carried out by placing the hydrogel in vacuum at an elevated temperature;
   l. the dehydration is carried out by heating the hydrogel in air or inert gas to elevated temperature, wherein
      i. the heating rate is slow,
      ii. the heating rate is fast, or
      iii. the heating follows the vacuum or air dehydration; and
   m. the dehydrated hydrogel is re-hydrated
      i. by placing in water, saline solution, Ringer's solution, salinated water, buffer solution, and the like,
      ii. by placing in a relative humidity chamber, or
      iii. by placing at room temperature or at an elevated temperature.

Each composition and attendant aspects, and each method and attendant aspects, which are described above can be combined with another in a manner consistent with the teachings contained herein.

The invention is further described by the following examples, which do not limit the invention in any manner.

EXAMPLES

1. Preparation of PVA/PEG Gelling Solution

Thirty grams of poly (vinyl alcohol) (PVA, MW=118,000) were added to 170 grams of cold deionized water and stirred while heating for about 2 hours to prepare a fully dissolved 15% (wt) PVA solution. The dissolved PVA solution was kept in an air convection oven (DKN600, Yamato) at 90° C. for about 16 hours. Poly (ethylene glycol) (PEG, MW=400) was heated to 90° C. in an air convection oven.

52.88 grams of hot PEG (at approximately 90° C.) was slowly mixed with 160 grams of hot (at approximately 90° C.) PVA solution by mechanical stirring while heating. This hot mixture of PVA and PEG is called a PVA/PEG gelling solution.

The gelling solution was poured into different size molds kept at 90° C. The molds were covered with an insulating blanket and left to cool down to room temperature. The solution formed a hydrogel upon cooling down to room temperature. Several batches of PVA/PEG solution was prepared to cast gels of different dimensions and sizes as described in Examples below.

In some of the examples, the gels that were cast were removed from the molds and subjected to further processing. In some examples the gels were used for testing and/or subjected to further processing in their "as-gelled" form; that is they contained PEG. In some of the examples the gels were first "dePEGed" and then used for testing and/or subjected to further processing in their "dePEGed" form. The "as-gelled" gel refers to the state where the gel was blot-dried right after removal from the mold. The "dePEGed" gel refers to the gel that was immersed in copious amounts of saline solution to remove PEG and hydrate the gel to equilibrium, which was confirmed gravimetrically.

2. Determination of the Equilibrium Water Content (EWC) in a Hydrogel

Following method was used to determine the equilibrium water content (EWC) in a hydrogel. The specimens were first immersed in saline solution with agitation for removal of any unbound molecules and for equilibrium hydration. To determine when the gels reached equilibrium hydration, their weight changes were recorded daily and the saline solution was replaced with fresh saline solution. After the equilibrium hydration level was reached, the equilibrium hydration weights of the specimens were recorded. Subsequently, the gel specimens were dried in an air convection oven at 90° C. until no significant changes in weight were detected. The EWC in a gel was then calculated by the ratio of the difference between the hydrated and dehydrated weights to the weight at equilibrated hydration state.

3. Uniaxial Compression of a Cylindrical Shaped PVA Hydrogel

Thirty grams of poly (vinyl alcohol) (PVA, MW=118,000) were added to 170 grams of cold deionized water and stirred while heating for about 2 hours to prepare a fully dissolved 15% (wt) PVA solution. The dissolved PVA solution was kept in an air convection oven (DKN600, Yamato) at 90° C. for about 16 hours. Poly (ethylene glycol) (PEG, MW=400) was heated to 90° C. in an air convection oven.

52.88 grams of hot PEG (at approximately 90° C.) was slowly mixed with 160 grams of hot (at approximately 90° C.) PVA solution by mechanical stirring. The mixture was kept at approximately 90° C. during stirring. The mixture solution was then poured into a hot mold kept at around 90° C. Several batches of PVA/PEG solution were prepared using this method to cast gels in a large mold.

The large mold was cylindrical in shape and was made out of PlexiGlass™ tube stock (Height: 50 mm, Diameter: 160 mm). One end of the tube was covered by glueing a piece of 7 mm thick PlexiGlass™ sheet. The mold was first heated in an air convection oven to approximately 90° C. and then topped-off (completely filled) with the hot PVA/PEG mixture that was also kept at approximately 90° C. The open top of the mold was covered by another piece of PlexiGlass™ sheet to minimize evaporation of water from the mixture and to create a smooth top surface. The mold was covered with an insulating blanket and cooled down to room temperature over 16 hours. Upon cooling, the PVA/PEG aqueous solution mixture formed a hydrogel. The hydrogel was removed from the mold. The height of the hydrogel was measured to be 46.8 mm and the diameter was 157.3 mm. The hydrogel typically shrinks during its formation and it is generally smaller than the mold in which it is cast.

The gel was removed from the mold, placed between two flat platens that were attached to an MTS machine (Mini-Bionix), and deformed. Thus, the deformation was carried out in the "as-gelled" form of the PVA hydrogel that contained both water and PEG (One can also remove PEG from the hydrogel by immersion in saline solution with agitation prior to deformation). The hydrogel was placed between the metal plates and compressed along the short axis of the cylinder. The compression proceeded at a rate of 0.2 mm/min to the point where the compression ratio was about 10. Compression ratio is defined as the ratio of the initial height to final height of the hydrogel. When the gel height under compression reached about 5 mm, the displacement was held constant for at least 24 hours to achieve stress relaxation equilibrium. Due to the large lateral expansion of the hydrogel during deformation, the circumference of the compressed hydrogel was extruded out of the platens' coverage before reaching the desired compression ratio. One can use slightly smaller diameter molds or increase the platens' diameter to prevent the extrusion.

Figure 4:
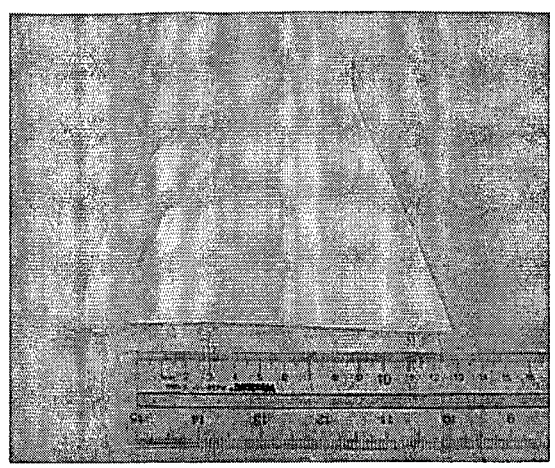
FIG. 4. The hydrogel was deformed and cut into 6 equal pieces; one is shown here. The deformed hydrogel was 8 mm thick at the center. Also note the "pizza-crust" shaped periphery caused by the extrusion of the gel.

The final height of the hydrogel in the center upon removal from compression was about 8 mm. A cut section of the gel is shown in FIG. 4.

A hydrogel implant with biaxial orientation of the molecules induced by uniaxial compression can be fabricated using the above described method. One would first determine the desired amount of compression ratio so that after deformation the thickness of the hydrogel can be at least equal to or larger than the thickness of the desired implant. The implant can either be machined at this stage from the deformed hydrogel sheet or the platens used during the deformation could have the shape of the inplant imprinted on their faces that make contact with the hydrogel so that after deformation the deformed hydrogel has the net or near-net shape of the implant. Additional machining steps is necessary at this stage, especially for the near-net shape implant.

4. Solvent Dehydration of Hydrogel

A hot PVA/PEG gelling solution was prepared as described in Example 1. The solution was poured into a hot mold kept at around 90° C. The mold was covered with an insulating blanket and was left to cool down to room temperature over 16 hours. Upon cooling a hydrogel block formed inside the mold. The mold dimensions were such that the hydrogel block had the shape of a sheet with dimensions of 7 mm×25 mm×45 mm. Several identical hydrogel sheets were thus fabricated.

The hydrogel sheets were cut into cylindrical test samples and these test samples were placed in different media to quantify the extent of equilibrium swelling and/or equilibrium deswelling by recording weight changes. The media used were saturated aqueous NaCl (5.2 M), saline (0.9% aqueous NaCl), acetone, iso-propyl alcohol, polyethylene glycol with a molecular weight of 400 g/mol (PEG400).

Cylindrical test samples were templated from the hydrogel sheets by cutting with a 9.5 mm diameter trephine. Five cylindrical test samples were used for each medium.

Weight and dimensions (diameter and height) of all pieces were first recorded in their "as gelled" form immediately after cutting with the trephine. Five test samples were then immersed in the respective media listed above. The samples were kept in glass vials filled with the respective media and shaken on a platform shaker at room temperature (Innova200 Platform Shaker, New Brunswick Scientific, Edison, N.J.). Weight and dimensions of all specimens were recorded in every 1 h for the first 8 h of immersion; and daily measurements continued until equilibrium swelling or deswelling was reached under continuous shaking. The hydrogel test samples swelled or deswelled to different degrees during storage in different media. Subsequently, all test samples were removed from the respective media and placed them in saline until equilibrium re-hydration was reached. The weight changes were recorded in every 1 hour for the first 8 hour of saline re-hydration and daily measurements continued until equilibrium hydration level was reached. The saline solution was changed daily to remove any of the other media that was coming out of the hydrogel test samples.

Swelling and/or deswelling values were calculated by dividing the difference between the weight at each measurement step and initial weight of the specimen by the initial weight of the specimen. In all cases, the initial weight was the weight recorded immediately after cutting the test samples with the trephine in their "as-gelled" form.

Figure 5:
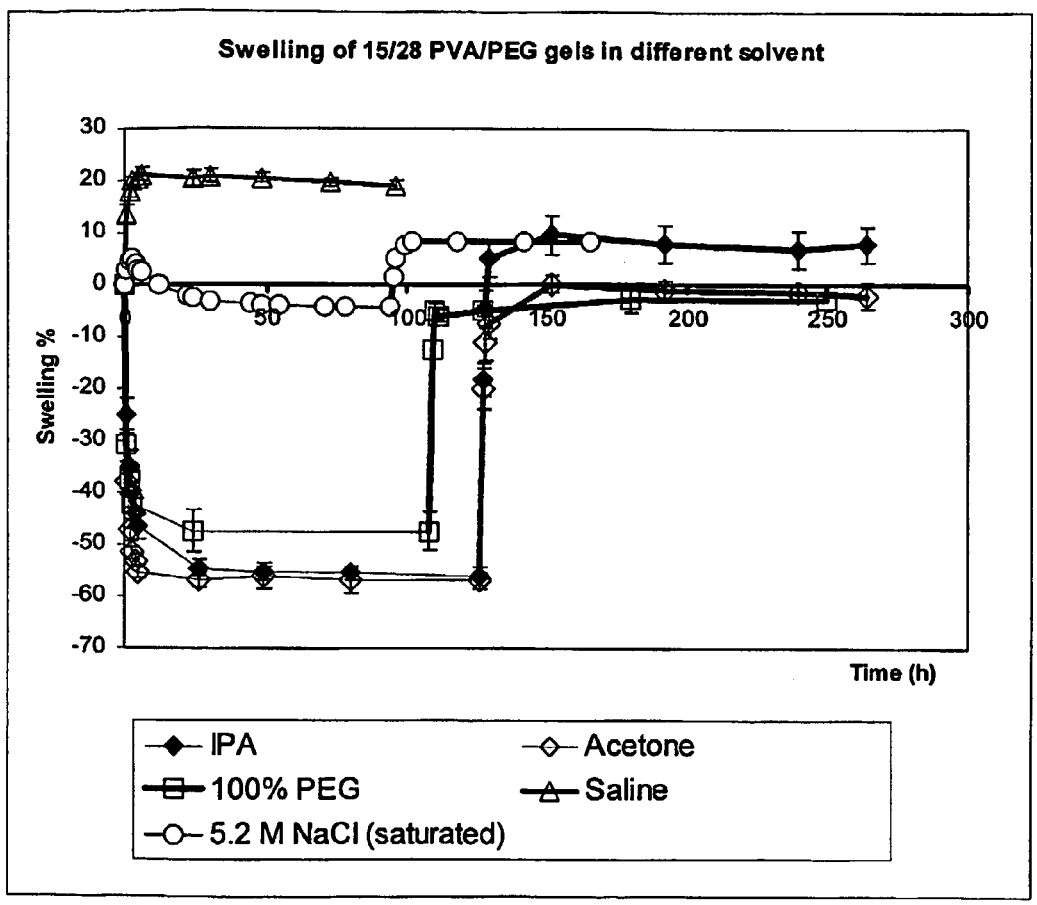
FIG. 5. Solvent dehydration for 15/28 PVA-PEG gels. The open markers are data collected during immersion in respective media and filled markers are data collected during the subsequent immersion in saline.

The hydrogel samples swelled in saline and saturated NaCl solution and deswelled in the other media (FIG. 5). The PEG400, acetone and IPA deswelled the hydrogel samples. The deswelling is attributed to loss of water to the surrounding medium. There was likely absorption of the medium in the hydrogels during the first phase, i.e. media immersion. When the samples were placed in saline, following media immersion, there was marked re-hydration. The equilibrium level of re-hydration was comparable with the hydrogel samples that were previously deswelled in acetone, PEG400, and saturated NaCl.

Equilibrium hydration levels of hydrogels can be reduced by immersion in certain media. Reduced hydration level improved the mechanical properties of the hydrogel.

One can fabricate an implant using the solvent dehydration technique described in this example. Dimensional changes caused by solvent dehydration and/or subsequent re-hydration would have to be taken into account so that final equilibrium dimensions achieved with the implant after it is implanted in vivo are the desired dimensions. Also the implant can be stored until implantation in a medium that can cause it to deswell and the implant can be inserted into the human body in its swollen state; bodily fluids can then rehydrate the implant to swell.

5. Channel Die Deformation of PVA Hydrogel

A hot PVA/PEG gelling solution was prepared as described in Example 1. The solution was poured into a hot mold kept at around 90° C. with a cover to form a hydrogel sheet. After one day of gelling at room temperature the hydrogel was removed from the mold. The dimensions of the hydrogel were 54 mm×44 mm×54 mm. Two such hydrogel blocks were fabricated. Upon removal from the mold, one of the hydrogel was immediately deformed in its "as-gelled" form. The second block was first immersed in saline solution with agitation (for de-PEGing; that is PEG removal and equilibrium hydration) and was deformed afterwards.

Figure 6:
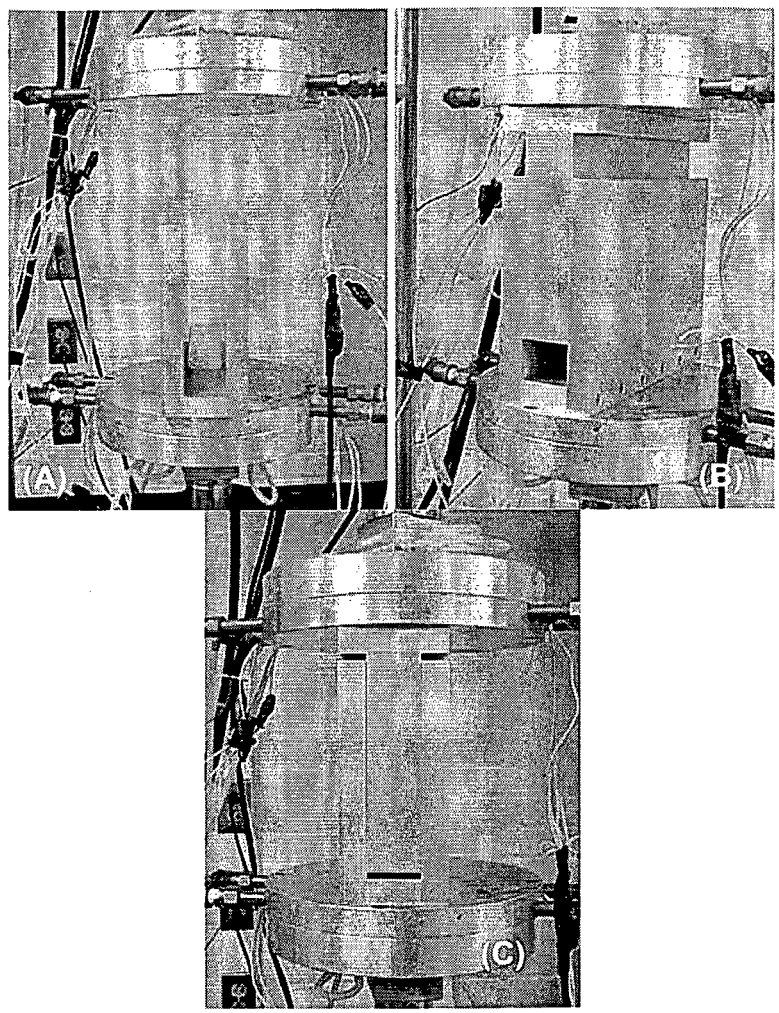
FIG. 6. (A) The hydrogel was placed inside the channel die for uni-directional compression. (B) The plunger was inserted in the die in contact with the hydrogel before compression. (C) The hydrogel inside the channel was compressed and the displacement was held until the stress relaxation reached equilibrium.

An aluminum channel die with inner channel dimensions of 12" length, 2" height, and 8" width was custom-manufactured. The die was placed between two parallel metal plates attached to an MTS loading frame (FIG. 6). The rectangular prism shaped hydrogel was placed in the center of the channel and the die plunger was kept in contact with the top surface of the hydrogel. The compression was carried out on an MTS machine (MTS servo-hydraulic testing machine, MTS, Minneapolis Minn.) and proceeded at a rate of 0.2 mm/min to the point where the compression ratio was about 10 (initial height:final height). When the hydrogel height under compression reached about 5 mm, the displacement was held constant to achieve stress relaxation.

Figure 7:
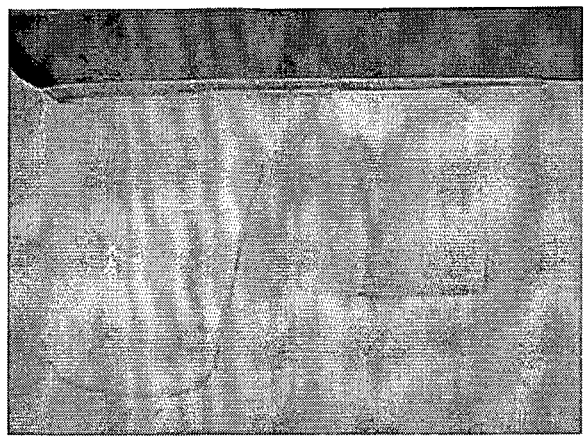
FIG. 7. On the right is a hydrogel prism prior to deformation and on the left is a representative channel-die deformed hydrogel prism, which had the same dimensions as the hydrogel shown on the right prior to deformation.

Upon completion of compression, the hydrogel was removed from the channel die (FIG. 7). The weight of the dePEGed hydrogel reduced from 124.4 g to 55.5 g, and its thickness was reduced from 54 mm to 6.6 mm. Even though the displacement of the plunger was such that the deformation resulted in 5 mm of thickness in the hydrogel block; upon removal of the load on the plunger, the deformed block recovered elastically to 6.6 mm.

The deformed gels were cut into 6 equal pieces to serve as samples that were subjected to other processing steps. Some of the samples were re-hydrated in saline at room temperature until equilibrium hydration was reached, which was confirmed gravimetrically. Some of the samples were vacuum dehydrated at room temperature until equilibrium dehydration was reached (confirmed gravimetrically), which took 5 days. Some of the samples were dehydrated by placing in polyethylene glycol (PEG400; MW=400 g/mol) until equilibrium dehydration was reached (confirmed gravimetrically), which took 2 days. Following the respective dehydration steps some of the samples were subjected to slow annealing and some to flash annealing at 160° C. Flash anneal was carried out in nitrogen at 160° C. by placing the dehydrated samples in an oven already heated to 160° C. for one hour (flash anneal). Slow annealing was carried out by heating from room temperature to 160° C. at approximately 5° C./min and subsequently keeping at 160° C. for a total annealing time of one hour (slow anneal). After annealing, flash or slow, all samples were immersed in saline until equilibrium hydration was reached, which was confirmed gravimetrically. Finally, the gels were analyzed to determine the EWC using the method described in Example 2.

Table 1 lists the equilibrium weight change and EWC of the channel-die deformed hydrogel sample following different processing schemes. Following deformation and re-hydration the gel showed a 36% weight loss, indicating loss of water. Additional experiments also showed that the extent of water loss increases with increasing extent of deformation; therefore one can tailor the equilibrium water content of deformed hydrogels by varying the extent of deformation. The PEG400 dehydration alone did not markedly affect the EWC. On the other hand, both of the annealing schemes substantially reduced the EWC. Lower EWC produced stronger and tougher gels. The strongest gels were achieved by vacuum dehydration followed by annealing of the channel-die deformed de-PEGed gels. One can fabricate a finished implant using any of the steps described above and tailor a desired EWC.

6. Deformation of PVA/PEG Gel Up to 90% Uniaxial Compression

A hot PVA/PEG gelling solution was made as described in Example 1. The solution was poured into a rectangular prism shaped mold (40 mm×45 mm×50 mm) kept at 90° C., the mold was covered and insulated with an insulating blanket. The mold was left to cool down to room temperature to form a hydrogel. Two such hydrogel blocks were prepared. One block was used in its "as-gelled" form and the other one was immersed in saline solution at room temperature for removal of PEG (dePEGing) and equilibrium hydration.

TABLE 1

Equilibrium weight change and EWC of the channel-die deformed hydrogel sample following different processing schemes.

| 15/28 PVA/PEG hydrogel that was dePEGed and then deformed in the channel-die followed by | Equilibrium weight change (%) (n = 1 each) | Equilibrium water content (%) (n = 3 each) |
|---|---|---|
| Vacuum dehydration, followed by slow annealing and subsequent re-hydration | −82.83 | 37.15 ± 0.032 |
| Vacuum dehydration followed by flash annealing and subsequent re-hydration | −83.29 | 37.02 ± 0.044 |
| Vacuum dehydration and subsequent re-hydration | −64.11 | 73.42 ± 0.042 |
| 100% PEG400 dehydration and subsequent re-hydration | −51.33 | 82.08 ± 0.886 |
| 100% PEG400 dehydration followed by slow annealing and subsequent re-hydration | −78.32 | 52.67 ± 4.222 |
| Re-hydration only | −35.97 | 83.24 ± 0.731 |

The rectangular prism shaped gel was placed between two flat metal plates attached to an MTS machine (MTS servo-hydraulic testing machine, MTS, Minneapolis Minn.) and compressed along the longest axis. The compression proceeded at a rate of 0.2 mm/min to the point where the compression ratio was 10 (initial height:final height). When the gel height under compression reached 5 mm, the displacement was held constant for at least 24 hours until stress relaxation equilibrium was achieved. The uniaxial compression allowed us to achieve a permanently deformed gel with biaxial orientation of the hydrogel molecules. Subsequent to the deformation the gel was removed from the MTS machine. There was some elastic recoil (recovery of elastic deformation) upon unloading; but the resulting gel had permanent deformation. The uniaxial deformation was carried out with both of the as-gelled and dePEGed hydrogels.

At this step a medical device, such as a joint (hip, knee, or shoulder) interpositional device, can be machined from the deformed PVA gel.

Upon completion of uniaxial compression, the dimensions of rectangular prism shaped "as-gelled" hydrogel specimen changed from a length of 41.83 mm, a width of 47.37 mm, and a height of 49.75 mm, to a length of 88.29 mm, a width of 98.74 mm, and a height of 6.4 mm. In the case of dePEGed hydrogel, the dimensions of the specimen changed from a length of 43.49 mm, a width of 50.01 mm, and a height of 53.03 mm to a length of 93.17 mm, a width of 97.78 mm, and a height of 6.71.

The deformed gels were cut into 5 pieces and each cut sample was subjected to further processing.

Some of the hydrogel specimens from the "as-gelled and deformed" group and "dePEGed and deformed" group were re-hydrated in saline at room temperature until equilibrium hydration was reached, which was confirmed gravimetrically. Some of the hydrogel samples from both groups were vacuum dehydrated at room temperature until equilibrium dehydration was reached (confirmed gravimetrically), which took 5 days. Some of the hydrogels of each group were dehydrated by placing in polyethylene glycol (PEG400; MW=400 g/mol) until equilibrium dehydration was reached (confirmed gravimetrically), which took 2 days. Following the respective dehydration steps some of the samples were subjected to slow annealing and some to flash annealing at 160° C. Flash anneal was carried out in nitrogen at 160° C. by placing the dehydrated samples in an oven already heated to 160° C. for one hour (flash anneal). Slow annealing was carried out by heating from room temperature to 160° C. at approximately 5° C./min and subsequently keeping at 160° C. for a total annealing time of one hour (slow anneal). After annealing, flash or slow, all samples were immersed in saline until equilibrium hydration was reached, which was confirmed gravimetrically. Finally, the gels were analyzed to determine the EWC using the method described in Example 2.

Tables 2-3 list the equilibrium weight change and the equilibrium water content (EWC) of the deformed hydrogel samples following different processing schemes. After deformation the as-gelled sample re-hydrated more than the dePEGed ones; presumably the presence of PEG in the as-gelled hydrogel protected the pore structure and prevented their collapse, which, in turn, improved the re-hydration capacity of the hydrogel. The EWC was higher in the as-gelled and deformed samples than it was in the dePEGed and deformed samples when re-hydration followed deformation immediately. Similarly, for all of the other processing schemes the as-gelled samples had higher EWC than the dePEGed samples. The PEG400 dehydration alone did not markedly affect the EWC. On the other hand, both of the annealing schemes substantially reduced the EWC. Lower EWC produced stronger and tougher gels. One can fabricate a finished implant using any of the steps described above and tailor a desired EWC.

TABLE 2

Equilibrium weight change and the EWC of the deformed hydrogel samples following different processing schemes.

| 15/28 PVA/PEG hydrogel that was dePEGed and then deformed followed by | Equilibrium weight change (%) (n = 1) | Equilibrium water content (%) (n = 3) |
|---|---|---|
| Vacuum dehydration followed by slow annealing and re-hydration | −75.22 | 51.97 ± 0.10 |
| Vacuum dehydration followed by flash annealing and subsequent re-hydration | −78.97 | 46.62 ± 0.19 |
| 100% PEG400 dehydration and subsequent re-hydration | −51.64 | 84.25 ± 5.038 |
| 100% PEG400 dehydration followed by slow annealing and subsequent re-hydration | −77.54 | 73.90 ± 3.461 |
| Re-hydration only | −50.20 | 86.06 ± 1.022 |

7. The Effect of PEG Concentration on the Deswelling of PVA Hydrogels

A hot PVA/PEG gelling solution was prepared as described in Example 1 and poured into a hot mold (7 mm Height×2.5 mm Diameter×4.5 mm Width) with a cover to form a hydrogel sheet. After 1 day of gelling at room temperature, the molded hydrogel sheet was cut into cylindrical gels using a trephine blade (Corneal trephine blades, Diameter 9.5 mm, Stradis Medical, Alpharetta, Ga.) mounted on a drill press (Enco Manufacturing Co, Model 105-1100, Chicago, Ill.). The initial height, diameter and weight of each cylindrical hydrogel sample were measured upon cutting. These cylindrical test samples are called "as-gelled" cylindrical test samples because they were not subjected to any treatment after gelling and they contained PEG that was in the gelling solution.

Some of the "as-gelled" samples were immersed in 100% poly-ethylene glycol with a molecular weight of 400 g/mol, (PEG400) and five additional "as-gelled" samples were immersed in a 50% PEG400 aqueous solution at room temperature with agitation. Immersion in PEG causes removal of water from the PVA hydrogel, thus results in dehydration and deswelling. The PEG immersion of the cylindrical test samples lasted for at least 24 hours to ensure equilibrated dehydration state.

TABLE 3

Equilibrium weight change and the EWC of the deformed hydrogel samples following different processing schemes.

| 15/28 PVA/PEG as-gelled hydrogel that was deformed followed by | Equilibrium weight change (%) (n = 1) | Equilibrium water content (%) (n = 3) |
|---|---|---|
| Vacuum dehydration followed by slow annealing and re-hydration | −80.18 | 73.57 ± 0.022 |
| Vacuum dehydration followed by flash annealing and subsequent re-hydration | −80.57 | 67.95 ± 0.028 |
| 100% PEG400 dehydration and subsequent re-hydration | −23.46 | 89.95 ± 0.698 |
| 100% PEG400 dehydration followed by slow annealing and subsequent re-hydration | −64.58 | 77.13 ± 2.778 |
| Re-hydration only | −8.09 | 91.56 ± 0.275 |

Five additional "as-gelled" cylindrical test samples were immersed in saline for removal of PEG from the hydrogels (dePEGing).

When the equilibrium deswelling of the hydrogel samples that were in 100% and 50% PEG400 was achieved, i.e., no significant changes in each hydrogel weight was detected, these hydrogel samples were removed from their respective media and placed in saline solution with agitation at room temperature for at least 2 days for re-hydration and removal of PEG from the hydrogel. The saline solution was replaced with fresh saline everyday during saline immersion of these samples. When equilibrium re-hydration of the hydrogel sample was obtained with no significant changes in weight over time, the final height, diameter and weight of the hydrogel specimens were recorded.

Gravimetric swelling and/or deswelling of the hydrogel samples after PEG immersion and subsequent re-hydration in saline was calculated with respect to the "as-gelled" state (see Table 4).

TABLE 4

Effect of PEG concentration on dehydration of PVA/PEG gels and subsequent re-hydration in saline.

| 15-28 As-Gelled PVA/PEG hydrogel samples after | % Weight change from the as-gelled state |
|---|---|
| 100% PEG 400 dehydration | −45.44 |
| 50% PEG400 dehydration | −26.76 |
| 100% PEG400 dehydration and re-hydration | −6.37 |
| 50% PEG400 dehydration and re-hydration | −3.11 |
| Re-hydration only | 11.31 |

The degree of deswelling in the hydrogel samples during PEG immersion was influenced by the concentration of the PEG solutions. The "as-gelled" hydrogels deswelled by about 45% in 100% PEG400 and by about 27% in 50% PEG400 solution. The gels immersed in 100% PEG had slight distortion in shape: The center regions in the top and bottom surfaces of each cylindrical hydrogel were slightly dimpled, probably due to non-uniform swelling rates in the core and the skin of the hydrogel. In contrast, the samples in the 50% PEG solutions had no discernible shape distortion after dehydration.

The samples that were swollen in 100% PEG and 50% PEG solutions, swelled after immersion in saline.

The observations of the present example are important for determining the storage protocol of hydrogel implants, such as those that can be used as mosaicplasty plugs or interpositional devices. For example, the gels that can reach the same or similar dimensions at the re-hydrated state can be previously reduced to various dimension ranges for ease of insertion into the body cavity, with minimal distortion in the hydrogel shape, by simply controlling the PEG concentration in the hydrogel storing solution.

8. The Effect of PEG Molecular Weight on Dehydration of PVA Hydrogels

A hot PVA/PEG gelling solution was prepared as described in Example 1 and poured into a hot mold kept at around 90° C. (7 mm Height×2.5 cm Diameter×4.5 cm Width) with a cover to form a hydrogel sheet. The mold was covered by an insulting blanket and was left to cool down to room temperature. After 1 day of gelling at room temperature, the molded hydrogel sheet was cut into cylindrical hydrogels using a trephine blade (Corneal trephine blades, Diameter 9.5 mm, Stradis Medical, Alpharetta, Ga.) mounted on a drill press. Height, diameter and weight of each cylindrical hydrogel specimen were measured upon cutting.

The hydrogel cylindrical samples were used in their "as-gelled" form. The "as-gelled" form is the form of the PVA hdyrogel that contains water and PEG that was present in the PVA/PEG gelling solution used.

The hydrogel samples were immersed in 50% aqueous solution of poly-ethylene glycol with different molecular weights (MW) to determine the effect of PEG MW on the extent of hydrogel deswelling.

Some of the cylindrical hydrogels were immersed in 50% PEG400 (PEG MW=400 g/mol) aqueous solution and some of the hydrogels were immersed in a 50% PEG600 (PEG MW=600 g/mol) aqueous solution at room temperature with agitation for at least 24 hours to ensure equilibrated deswelling state. Some of the hydrogels were immersed in saline with no PEG deswelling to serve as controls. Immersion in 50% PEG400 or 50% PEG600 solution resulted in weight loss in the hydrogel samples likely due to the removal of water; hence the immersion of the hydrogel samples in 50% PEG solutions caused deswelling.

When the deswelling of the hydrogel samples reached equilibrium i.e., no significant changes in hydrogel weight were detected over time, the hydrogel specimens were placed in saline solution with agitation at room temperature for at least 2 days for re-hydration and removal of PEG from the hydrogel samples. The saline solution was replaced with fresh saline everyday during immersion to remove the PEG that was eluting out of the hydrogel samples. When equilibrium re-hydration of the hydrogel was obtained with no significant changes in weight over time, the hydrogel samples were removed from the saline solution, blot-dried, and the final height, diameter and weight of the hydrogel specimens were recorded. Gravimetric swelling and/or swelling of the hydrogel after PEG dehydration and subsequent re-hydration in saline was calculated with respect to the "as-gelled" state (see Table 5). That is the percent deswelling or percent swelling of the hydrogel at a given step is the ratio of the difference between the weight of the hydrogel at that step and the "as-gelled" weight to the weight of the "as-gelled" sample.

The molecular weight of PEG in the 50% aqueous PEG solutions used during immersion slightly affected the extent of deswelling of the "as-gelled" hydrogel samples. The "as-gelled" hydrogel samples deswelled by 27% in 50% aqueous PEG400 and by 31% in 50% aqueous PEG600 solutions. The higher the PEG MW was, the more deswelled the PVA hydrogels were after the PEG immersion. PEG with a molecular weight higher than 600 g/mol would exhibit more deswelling of the hydrogels. The dehydrated hydrogels both in 50% PEG400 and in 50% PEG600 showed no discernible distortion in shape.

TABLE 5

Effect of PEG MW on dehydration of "as-gelled" PVA/PEG hydrogels and subsequent re-hydration.

| 15-28 As-Gelled PVA/PEG hydrogel samples after | % Weight change from the as-gelled state |
| --- | --- |
| 50% PEG 400 dehydration | −26.76 |
| 50% PEG 600 dehydration | −30.51 |
| 50% PEG 400 dehydration and re-hydration | −3.11 |
| 50% PEG 600 dehydration and re-hydration | −3.53 |
| Re-hydration only | 11.31 |

A hydrogel implant can be fabricated and immersion in different media can be used to tailor mechanical properties and control dimensions of the implant. One such method is to immerse the implant in aqueous solutions of PEG with different molecular weights. The above method can also be used by first removing the PEG from the hydrogel (immersion in saline with agitation—dePEGing) and then immersing it in the PEG solutions.

9. The Effect of the Presence of PEG in PVA Hydrogel on the Hydrogel's Capacity to Rehydrate Subsequent to Dehydration A hot PVA/PEG gelling solution was prepared as described in Example 1 and was cast in rectangular molds (44 mm×54 mm) to prepare sheets of thickness of either 7 mm or 21 mm. The molds were covered with an insulating blanket and left to cool down to room temperature over 16 hours. Hydrogels were thus formed in these molds.

Four of each thickness (7 mm and 21 mm) hydrogel sheets were immersed into saline for removal of PEG (dePEGing) (Set I) and another set of four was kept in its "as-gelled" form (Set II). The hydrogel specimens in both sets were first weighed and subsequently placed in vacuum at room temperature for dehydration. The weight changes were recorded daily until equilibrium dehydration level was reached (5 days for "as-gelled" Set II and 7 days for the dePEGed Set I). After vacuum dehydration, one sample from each Set was immersed directly in saline for re-hydration. The weight changes were recorded daily until equilibrium re-hydration level was reached (5-6 days).

Another set of 7 mm hydrogel sheets (Set III) were used to study the effect of room temperature air dehydration. For this experiment, three hydrogel sheets were weighed and then left in air at room temperature (approximately 24° C.) for up to 9 days. The weight change of the samples was recorded daily.

An additional set of hydrogel sheets (Set IV) were used to study the effect of room temperature air dehydration following PEG removal from the hydrogel sheets. For this experiment, three hydrogel sheets were dePEGed in saline at room temperature with agitation until equilibrium hydration level was reached (approximately 6 days). Subsequently the hydrogel sheets were weighed and left in air at room temperature for up to 9 days. The weight change was recorded daily.

Subsequent to vacuum dehydration, one sample from each of Set I and Set II was annealed in nitrogen at 160° C. by placing in an oven already heated to 160° C. for one hour (flash anneal). The sample's weight and dimensions were recorded before and after annealing. Another sample from each set was annealed by heating from room temperature to 160° C. at approximately 5° C./min and subsequently keeping at 160° C. for a total annealing time of one hour (slow anneal). After annealing, flash or slow, all samples were immersed in saline until equilibrium hydration. The weight and dimension of the samples were recorded daily.

The equilibrium water content of the 21 mm thick PVA-PEG as-gelled and dePEGed were measured at different processing steps. To this end, three samples were cut from each of the (1) vacuum dehydrated and subsequently re-hydrated, (2) vacuum dehydrated, then slow annealed and subsequently re-hydrated and (3) vacuum dehydrated, then flash annealed, and subsequently re-hydrated gels. The equilibrium weights of all samples were determined and then they were placed in a convection oven at 90° C. The weight measurements of each sample continued, twice in the first day of oven drying and daily thereafter for 3 days. All samples reached equilibrium after 1 day of oven drying. The equilibrium dry weights of the samples were used to calculate the water content in the three groups of equilibrium re-hydrated gels.

Figure 8:
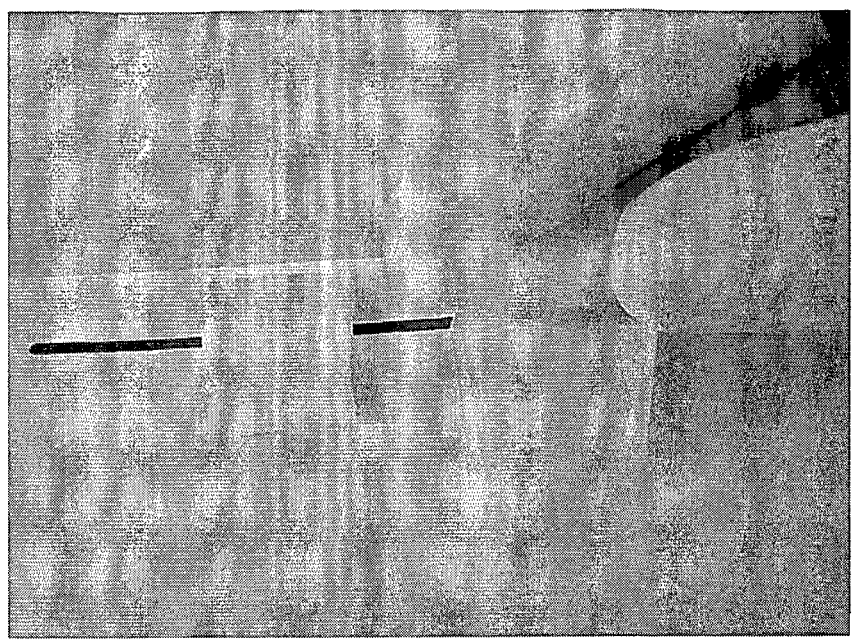
FIG. 8. The difference in the appearance of "as-gelled" on the left and dePEGed samples on the right after vacuum dehydration for the 7 mm thick samples.

FIG. 8 shows the difference in the appearance of the "as-gelled" and dePEGed samples after vacuum dehydration for the 7 mm samples. The starting hydrogel samples were opaque prior to the vacuum dehydration step. The hydrogel that was dePEGed prior to vacuum dehydration turned translucent after vacuum dehydration, while the one that was vacuum dehydrated in its "as-gelled" form retained its opaqueness. This change in appearance is attributed to the retention of the pore structure in the "as-gelled" samples during vacuum dehydration. The presence of PEG in the "as-gelled" samples appears to have protected the pores from collapsing by occupying the porous space in the hydrogel during vacuum dehydration. PEG is not a volatile molecule, hence remained in the structure while water evaporated out of the samples during vacuum dehydration. In contrast, dePEGing removed the PEG and left the porous structure of these hydrogel samples filled with water only. Evaporation of the water resulted in evacuation of the pores and eventual collapse of the hydrogel during vacuum dehydration, thus making these samples appear more translucent.

The vacuum dehydration progressed at a much faster rate than the air dehydration; the rate of weight loss was faster in vacuum and the samples left in vacuum reached equilibrium dehydration or deswelling levels faster than the samples left in air. The equilibrium dehydration values reached with either method were still comparable. Therefore, one can choose either method of dehydration.

Tables 6-7 show the extent of equilibrium re-hydration levels reached after various processing steps of the 7 mm as-gelled and dePEGed hydrogels. After the vacuum dehydration, the equilibrium re-hydration level was much higher than those achieved by the hydrogels that were treated by either slow or flash annealing steps. In the as-gelled group the flash annealing step resulted in the least amount of re-hydration. The dePEGed samples showed less re-hydration than their as-gelled counterparts.

Figure 9:
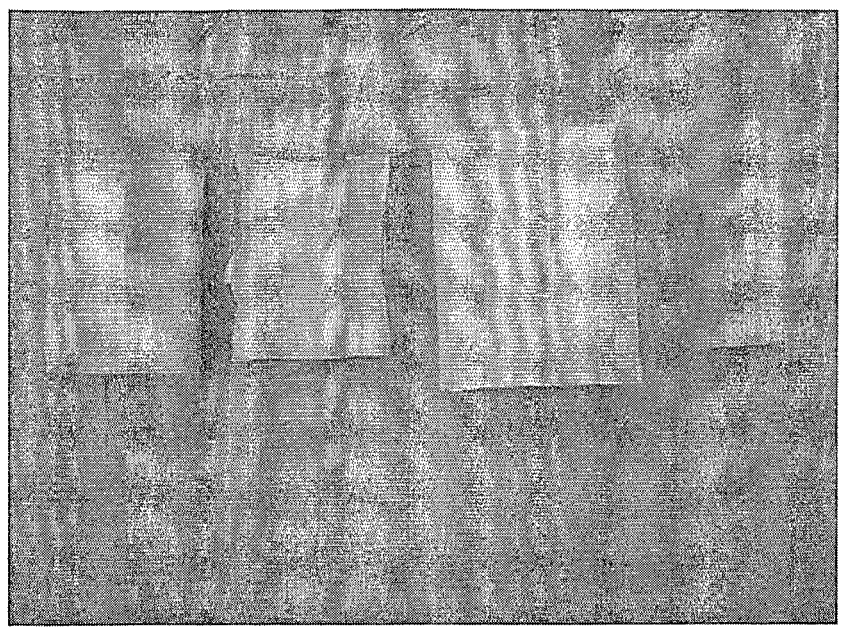
FIG. 9. This figure shows the 21-mm thick hydrogels in the following forms: From left to right, the "as-gelled" hydrogel, the "as-gelled" hydrogel that was subsequently dehydrated in vacuum, the "as-gelled" hydrogel after 6 days of dePEGing, the dePEGed hydrogel that was vacuum dehydrated. All samples started with the same sample size.

FIG. 9 shows the 21 mm hydrogel sheets at various steps of processing. The presence of PEG in the as-gelled form of the hydrogel resulted in substantially less deswelling in volume upon vacuum dehydration than was the case with the dePEGed gel that did not contain any PEG.

Tables 8-9 show the extent of equilibrium re-hydration levels reached after various processing steps of the 21 mm as-gelled and dePEGed hydrogels. After the vacuum dehydration, the equilibrium re-hydration level was much higher than those achieved by the hydrogels that were treated by either slow or flash annealing steps. In the as-gelled group the flash annealing step resulted in the least amount of re-hydration. The dePEGed samples showed less re-hydration than their as-gelled counterparts.

TABLE 6

Shows the extent of equilibrium re-hydration levels reached after various processing steps of the 7 mm as-gelled and dePEGed hydrogels.

| 7 mm thick as-gelled samples | % Weight change from the as-gelled state |
| --- | --- |
| Vacuum dehydration only | −62.6 ± 0.12 |
| Vacuum dehydration and slow annealing | −63.6 ± 0.18 |
| Vacuum dehydration and flash annealing | −65.8 ± 0.21 |
| Vacuum dehydration and re-hydration | −4.16 ± 0.19 |
| Vacuum dehydration slow annealing and re-hydration | −25.8 ± 0.10 |
| Vacuum dehydration subsequent flash annealing and re-hydration | −48.4 ± 0.11 |

TABLE 7

Shows the extent of equilibrium re-hydration levels reached after various processing steps of the 7 mm as-gelled and dePEGed hydrogels.

| 7 mm thick dePEGed samples | % Weight change from the as-gelled state |
| --- | --- |
| DePEGed in saline | 18.1 ± 0.19 |
| Vacuum dehydration only | −85.6 ± 0.23 |
| Vacuum dehydration and slow annealing | −86.7 ± 0.18 |
| Vacuum dehydration and flash annealing | −86.9 ± 0.26 |
| Vacuum dehydration and re-hydration | −67.7 ± 0.25 |
| Vacuum dehydration slow annealing and re-hydration | −81.8 ± 0.28 |
| Vacuum dehydration subsequent flash annealing and re-hydration | −82.5 ± 0.18 |

The as-gelled samples showed substantially higher re-hydration levels at each one of the dehydration steps than the dePEGed samples. The equilibrium re-hydration levels after vacuum dehydration were −6.3% and −47.4% for the as-gelled and dePEGed gels, respectively. The equilibrium re-hydration levels after vacuum dehydration and flash annealing steps were −42% and −80% for the as-gelled and dePEGed gels, respectively. This is in further evidence for the protective effect of PEG in preventing the collapse of the porous structure during dehydration. This in turn allowed higher re-hydration capacity subsequent to the dehydration steps with the as-gelled hydrogels; while the dePEGed samples showed lower re-hydration capacity after vacuum or vacuum followed by annealing dehydration steps.

TABLE 8

Shows the extent of equilibrium re-hydration levels reached after various processing steps of the 21 mm as-gelled and dePEGed hydrogels.

| 21 mm Thick As-Gelled Samples | % Weight change from the as-gelled state |
| --- | --- |
| Vacuum dehydration only | −61.3 |
| Vacuum dehydration and slow annealing | −62.2 |
| Vacuum dehydration and flash annealing | −63.0 |
| Vacuum dehydration and re-hydration | −6.3 |
| Vacuum dehydration slow annealing and re-hydration | −31.6 |
| Vacuum dehydration subsequent flash annealing and re-hydration | −42.0 |

TABLE 9

Shows the extent of equilibrium re-hydration levels reached after various processing steps of the 21 mm as-gelled and dePEGed hydrogels.

| 21 mm Thick DePEGed Samples | % Weight change from the as-gelled state |
| --- | --- |
| DePEGed in saline | 19.1 |
| Vacuum dehydration only | −82.2 |
| Vacuum dehydration and slow annealing | −86.3 |
| Vacuum dehydration and flash annealing | −85.5 |
| Vacuum dehydration and re-hydration | −47.4 |
| Vacuum dehydration slow annealing and re-hydration | −80.1 |
| Vacuum dehydration subsequent flash annealing and re-hydration | −80.0 |

One can use one or several or all of the above methods to prepare hydrogel stock material that can be used to machine a hydrogel implant. One can also start with an implant that is shaped appropriately so that the dimensional changes encountered during processing can be accounted for to arrive at the desired implant size and shape. That implant can be subjected to one or several or all of the above methods, to make a net-shape or near-net shape implant.

Table 10 shows equilibrium water content (EWC) of the 21 mm PVA/PEG gels after various processing steps. The EWC of the re-hydrated samples were lower in the samples that had been subjected to annealing following vacuum dehydration. The vacuum dehydration is an essential step before annealing in that heating a hydrated gel to above 90° C. to cause melting of the gel; but vacuum dehydration elevates the melting point of the gels and allows annealing without melting. The dePEGed samples showed lower EWC than their as-gelled counterparts.

TABLE 10

Shows equilibrium water content (EWC) of the 21 mm PVA/PEG gels after various processing steps.

| | Equilibrium water content (%) |
| --- | --- |
| 21 mm As-Gelled Samples | |
| Vacuum dehydration slow annealing and re-hydration | 82.73 |
| Vacuum dehydration subsequent flash annealing and re-hydration | 74.34 |
| Vacuum dehydration and re-hydration | 87.05 |

TABLE 10-continued

Shows equilibrium water content (EWC) of the 21 mm PVA/PEG gels after various processing steps.

| | Equilibrium water content (%) |
|---|---|
| 21 mm dePEGed Samples | |
| Vacuum dehydration slow annealing and re-hydration | 45.73 |
| Vacuum dehydration subsequent flash annealing and re-hydration | 46.70 |
| Vacuum dehydration and re-hydration | 76.64 |

During the EWC measurements it was noticed that the 21 mm thick hydrogel sheets formed a skin layer with different properties than the bulk of the sheets. The skin appeared to be tougher than the bulk. Therefore, additional EWC measurements in the skin (within the first 3 mm of the free surfaces), at about 5 mm below the surface (Mid), and at about 10 mm below the surface (Core) were carried out. Table 11 shows the EWC values measured at these depths for both of the as-gelled and dePEGed 21-mm hydrogel sheets at different processing steps. The presence of skin was more apparent with the dePEGed sample, which showed a lower EWC in the skin than the bulk. One can use the annealing process to create a gradient of properties in the hydrogel. The rate of heating affects the thickness of the skin layer and dictates how sharp the gradient can be. The gradient is expected to be smoother with slower heating rate.

10. PEG Treatment of Deformed PVA Gel

A deformed gel was prepared as described in Example 1 and was deformed in the Carver Press as described in Example 5. Subsequent to the removal of the deformed gel from the Carver Press, the deformed gel was immersed in 100% PEG400 liquid at room temperature with agitation for 24 hours. Immersion in PEG400 resulted in partial to complete removal of water from the gel and hence partial to complete dehydration of the gel. The gel height that was 6.2 mm upon removal from the deforming press; and was subsequently decreased to 4.36 mm after immersing in PEG for 24 hours. Following the PEG dehydration, the deformed gel was placed in saline solution with agitation either at room temperature or at 37° C. for re-hydration and removal of PEG from the gel. At this step a medical device, such as a joint (hip, knee, or shoulder) interpositional device, can be machined from the PVA gel.

TABLE 11

Shows the EWC values measured at these depths for both of the as-gelled and dePEGed 21-mm hydrogel sheets at different processing steps.

| Samples | Skin | Mid | Core |
|---|---|---|---|
| As-Gelled, vacuum dehydrated and re-hydrated only | 86.56 | 86.98 | 87.04 |
| As-Gelled, vacuum dehydrated, slow annealed and re-hydrated | 83.26 | 82.88 | 83.45 |
| As-Gelled, vacuum dehydrated, flash annealed and re-hydrated | 80.76 | 80.10 | 78.62 |
| DePEGed, vacuum dehydrated and re-hydrated only | 65.24 | — | 81.61 |
| DePEGed, vacuum dehydrated, slow annealed and re-hydrated | 46.23 | — | 52.88 |
| DePEGed, vacuum dehydrated, flash annealed and re-hydrated | 45.96 | — | 55.78 |

11. Additional Deformation of 90% Uniaxially Compressed PVA/PEG Gel Within a Shaped Mold A deformed gel was prepared and subsequently underwent PEG-treatment as described in Example 10. The re-hydrated deformed gel was placed between the top and the bottom pieces of a shaped mold.

Figure 10:
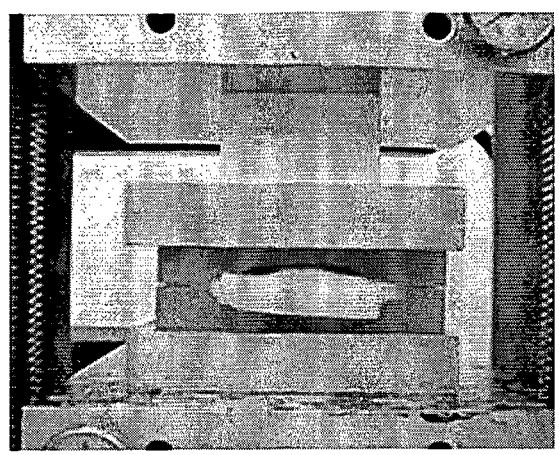
FIG. 10. (A) Shows additional deformation of deformed PVA/PEG gel sandwiched between the shaped molds. Note that the two parts of the mold made contact with each other at the end of the deformation. The excess hydrogel that squeezed out of the molds was discarded. (B) Shows the shaped molds and the final form of the deformed and shaped hydrogel gel that contoured to the shaped mold.
Figure 10:
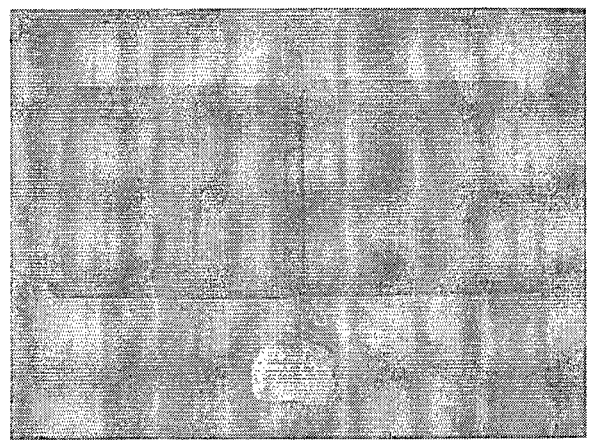
Figure 19:
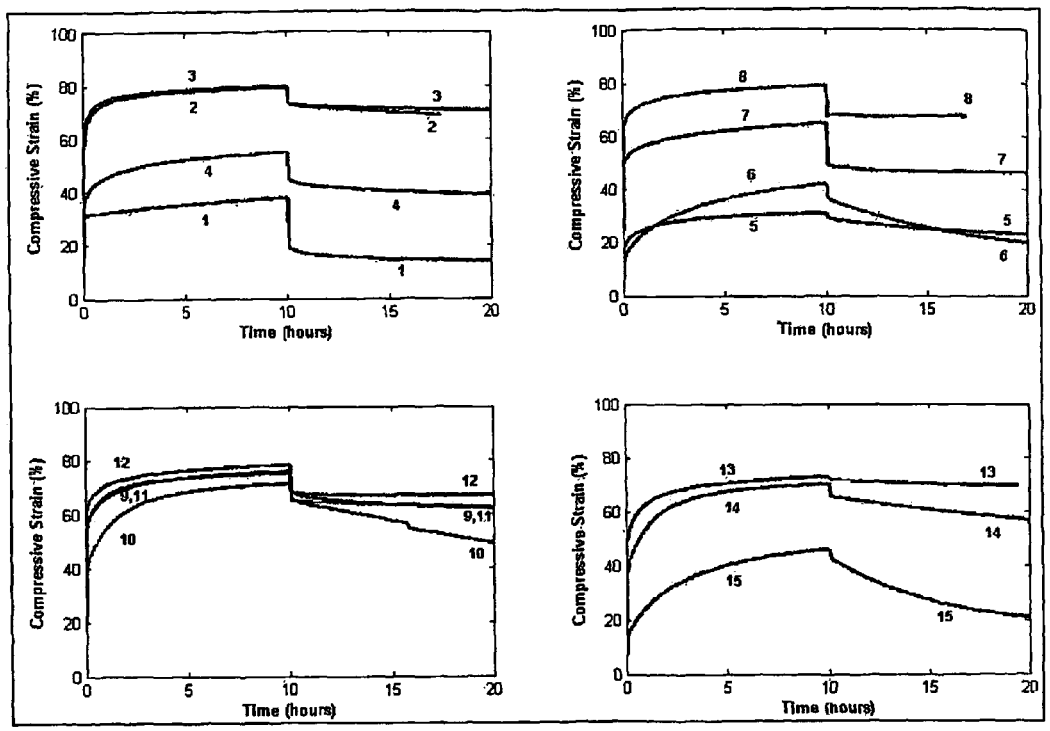
FIG. 19. Creep behavior is characterized in the Strain vs. Time plots above for the 10 hour loading and unloading cycles respectively. The sample numbers can be referred to from the Table 22. The samples 2, 8 and 13 were stopped before the end of the 10-hour unloading cycle.

The gel and mold were pressed together in the Carver Press until the top mold and bottom molds were in contact, allowing the gel in the middle to conform to the inner shape of the mold (see FIG. 10). The deformed hydrogel that was sandwiched between the shaped molds was kept under constant deformation for 24 hours. Subsequently, the deformed hydrogel was removed from the mold and further PEG-treated by immersion in 100% PEG400 for 24 hours. After removal from the PEG400, the deformed hydrogel was placed in saline solution at room temperature to reach equilibrium hydration level. The hydrogel retained its molded shape through each step including the step at which it was in its equilibrium hydration. The final gel obtained a shape of interpositional device (FIG. 19).

12. Effects of Single PEG-Immersion and Sequential PEG-Immersions

A hot PVA/PEG gelling solution was prepared as described Example 1 and poured into a hot mold (7 mm H×2.5 mm D×4.5 mm W) with a cover to form a hydrogel sheet. After 1 day of gelling at room temperature, the molded hydrogel sheet was cut into cylindrical hydrogels using a trephine blade (Diameter 9.5 mm) mounted on a drill press. Height, diameter and weight of each cylindrical hydrogel specimens were measured upon cutting in their "as-gelled" form. The hydrogel subsequently treated by immersion into polyethylene glycol with a molecular weight of 400 g/mol (PEG400). Some of the hydrogels were treated by a single PEG immersion step and other by multiple immersion steps with re-hydration in saline between the steps.

For single PEG immersion, the hydrogel cylinders cut from the molded hydrogel sheet were immersed in 100% PEG400 in their "as-gelled" state, with constant mechanical agitation. Five out of 70 hydrogel specimens were taken out from PEG400 liquid at each of the following time-steps: 1, 2, 3, 4, 5, and 6 hours, as well as 1, 2, 3, 4, and 6 days. At each time-step the height, diameter and weight of the hydrogel specimens were recorded after blot-drying. The percent decrease in the weight of each hydrogel specimen was calculated at each one of the time-steps. The "as-gelled" weight of the specimens was used as the initial weight for the percent weight loss calculation. Upon removal from PEG400 liquid, the specimens were re-hydrated in saline. And the percent change in the weight of the re-hydrated hydrogel specimens from their "as-gelled" state was calculated.

In the sequential PEG immersion, hydrogel cylinders were subjected to PEG immersion either in the "as-gelled" state or "dePEGed" state.

For the "dePEGed" group, upon removal from the mold, the hydrogel specimens were first immersed in saline solution with agitation for at least 2 days for removal of PEG and equilibrated hydration. At this step the weight and dimensions of the specimens were recorded and subsequently they were immersed in PEG400.

Both of the "as-gelled" hydrogel cylinders and the "dePEGed" hydrogel cylinders were immersed in 100% PEG400 liquid at room temperature with agitation for at least 24 hours to ensure equilibrated dehydration in each hydrogel specimen. Subsequent to the PEG-dehydration, the specimens were immersed in saline solution at room temperature with agitation for at least 2 days for PEG removal and to reach equilibrium re-hydration. This completed one cycle of single PEG-dehydration/re-hydration procedure. The same hydrogels were subjected to additional PEG-dehydration/re-hydration steps (total of three sequential dehydration/re-hydration steps). The height, diameter and weight of the hydrogel specimens were recorded after blot-drying after each step of dehydration and re-hydration.

The percent change in the weight of each hydrogel specimen was calculated at each one of the dehydration and re-hydration for both the "as-gelled" and "dePEGed" groups. In both groups, the "as-gelled" weight of the specimens was used as the initial weight for the percent weight loss calculation.

Figure 11:
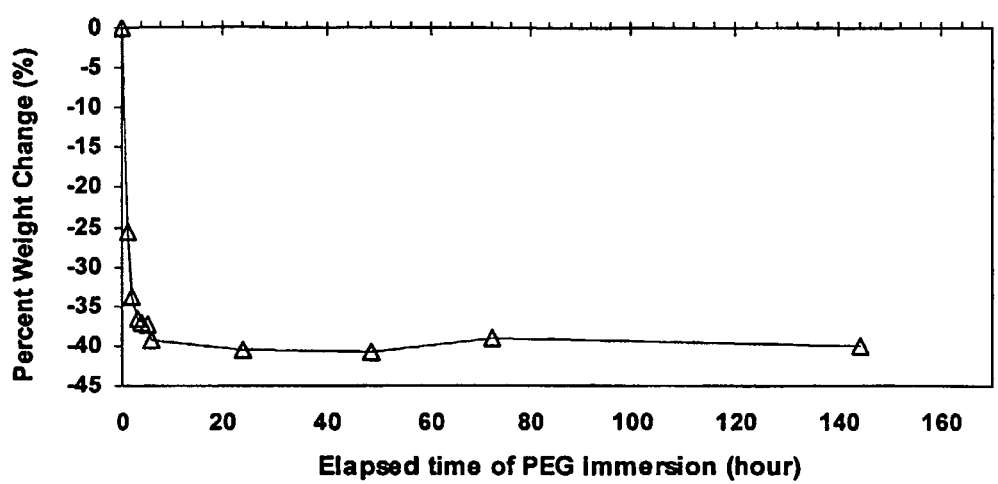
FIG. 11. The weight loss of an "as-gelled" hydrogel specimen during 100% PEG400 immersion is shown here. Note that equilibrium dehydration was reached in less than 24 hours.

As shown in FIG. 11, the PVA hydrogels immersed in 100% PEG400 experienced rapid gravimetric deswelling, which closely reached an equilibrium weight loss of about −40% within 6 hours of immersion. After one-day of immersion in PEG400, the hydrogel cylinders reached equilibrium deswelling with negligible variation in the weight of the specimens thereafter. Therefore, the maximum amount deswelling that can be achieved from a single PEG immersion was −40%.

Increasing levels of equilibrium deswelling were observed with the sequential PEG immersion and re-hydration steps with both of the "as-gelled" and "dePEGed" groups (Table 12). In the "as-gelled" group, the equilibrium deswelling was about −45% during the first PEG immersion; this value went down to −71% during the second PEG immersion and to about −76% during the third PEG immersion step. The difference in the equilibrium deswelling in comparison with the previous step decreased with increasing number of dehydration/re-hydration cycles. Upon completion of three sequential PEG immersion cycles including the final equilibrium re-hydration in saline, there was a −36% permanent gravimetric deswelling of the "as-gelled" PVA hydrogels. The hydrogel samples that were hydrated in saline with no prior PEG treatment showed a weight gain (swelling) of about +15%. In comparison the sequentially PEG treated hydrogel samples showed substantial densification and they appeared mechanically stronger.

TABLE 12

The weight percent change of the "as-gelled" PVA hydrogels at different steps of processing is shown.

| | Percent weight change (%) | | | | |
| --- | --- | --- | --- | --- | --- |
| | | | Sequential immersion | | |
| Measurement made | No PEG immersion | Single immersion | $1^{st}$ cycle | $2^{nd}$ cycle | $3^{rd}$ cycle |
| After equilibrium dehydration in PEG | NA | −40.48 | −45.44 | −71.58 | −75.93 |
| After equilibrium hydration in saline solution | +14.47 | −4.58 | −6.374 | −27.54 | −36.01 |

The percent weight change of the hydrogels was calculated with respect to the "as-gelled" weight. For example, (−) sign denotes deswelling (loss of weight) from the original "as-gelled" state, whereas (+) sign denotes swelling (gain of weight) from the "as-gelled" state.

The "dePEGed" specimen group showed more rapid gravimetric deswelling in every PEG immersion step than the "as-gelled" group. The equilibrium re-hydration achieved in saline at the end of each PEG immersion cycle was also lower in the "dePEGed" group than the "as-gelled" group. The "dePEGed" specimens showed a similar behavior as that of the "as-gelled" group, with a continuous decrease in the dehydration level with increasing number of PEG immersion/ saline re-hydration steps.

13. Pin-on-Disk (POD) Wear Testing with a Hydrogel Plug Articulating Against Animal Cartilage Forty grams of poly (vinyl alcohol) (PVA, MW=115,000 g/mol) were added to 160 grams of cold deionized water and stirred while heating for about 2 hours to prepare a fully dissolved 20% (wt) PVA solution. The dissolved PVA solution was kept in an air convection oven (DKN600, Yamato) at 90° C. for about 16 hours. Poly (ethylene glycol) (PEG400, MW=400 g/mol) was heated to 90° C. in an air convection oven.

62.22 grams of hot PEG400 (at approximately 90° C.) was slowly mixed with 200 grams of hot (at approximately 90° C.) PVA solution by mechanical stirring while heating. The mixture solution was then poured into a hot mold. Several batches of PVA/PEG solution was prepared to cast gels of different dimensions and sizes.

The hot PVA-PEG mixed solution was poured into a hot mold (7 mm H×25 mm D×45 mm W) with a cover to form a hydrogel sheet. Other molds with various thickness, such as 8 mm and 9 mm, were also used to fabricate thicker hydrogel sheets. After 1 day of gelling at room temperature, the molded hydrogel sheets were cut into cylindrical hydrogels using trephine blades (Diameter 6.5 mm or 7.0 mm) mounted on a drill press. Height, diameter and weight of each cylindrical hydrogel specimens were measured upon cutting and served as the weight and dimensions of the "as-gelled" reference.

Some of the cylindrical hydrogels were immersed either in 50% PEG400 aqueous solution or in 100% PEG400 liquid at room temperature with agitation for at least 24 hours to partially remove water from the hydrogel plugs. Partial dehydration resulted in reduction of the dimension and weight of the hydrogel plug. This shrinkage was used to facilitate the insertion of the plug to the cylindrical cavity in the cartilage. The hydrogel plug used in this example in particular was dehydrated in 100% PEG400.

Figure 12:
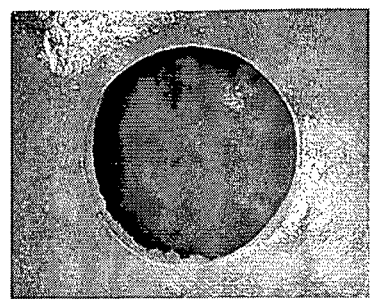
FIG. 12. Top-view optical micrograph of the cylindrical defect cavity drilled in the bovine knee cartilage.

An adult cow knee (left side) was used for the animal POD model. It was confirmed with x-rays that the knee had good bone stock. The soft tissue around the patella and distal femur was removed. Subsequently, two cartilage specimens 30 mm×15 mm×15 mm were cutout of the trochelar groove with a bandsaw and were used as an articular pair on a bi-directional pin-on-disk (POD) wear tester. The subchondral bone on the backside of the cut pieces of the cartilage was roughened with a drill and cemented onto the stainless steel holders with Surgical Simplex P bone cement (Stryker Howmedica Rutherford, N.J.). The holders were attached to the POD and loaded to determine the contact area between the two cartilage specimens. A defect was created on the top cartilage piece using a 5.0 mm diameter drill followed by a flat bottom drill to form an approximate 6.5 mm deep cylindrical cavity. The defect was within the contact area. The final dimension of the cavity was measured as 5.2 mm in diameter, and about 6.7 mm in depth (FIG. 12).

Pressure sensitive Fuji film was used to determine the contact area and contact pressure under an axial load of 890N. The Fuji film was placed between the cartilage surfaces and load was applied for 2 minutes. The average pressure was 5.0-6.0 MPa.

The bottom cartilage piece was mounted on the bi-directional POD, which moved it on a 5 mm×10 mm rectangular track at 0.5 Hz using an X-Y table (Parkers Systems, Rohnert Park, Calif.). The test was run in 100% bovine serum environment. The serum was mixed with penicillin-streptomycin prior to the test to delay bacterial growth and to protect the cartilage. The table was mounted on an MTS servo-hydraulic testing machine (MTS, Minneapolis Minn.). The load was applied as double-peak Paul-type load curve with a peak load of 890N and a preload of 90N (Bragdon et al. *Journal of Arthroplasty*, 2001. 16(5): p. 658-65.)

As shown in Table 13, the initial dimensions of the hydrogel plug (Table 13) cut from the hydrogel sheet were intentionally somewhat larger than those of the cavity (Table 13). Initially the hydrogel plug was about 6.53 mm in diameter and 8.76 mm in height and the dimensions of the cavity were about 5.2 mm in diameter and about 6.7 mm in height. The dehydration of the hydrogel plug in 100% PEG for temporary dimensional shrinkage helped in insertion of the plug into the cartilage cavity.

Figure 13:
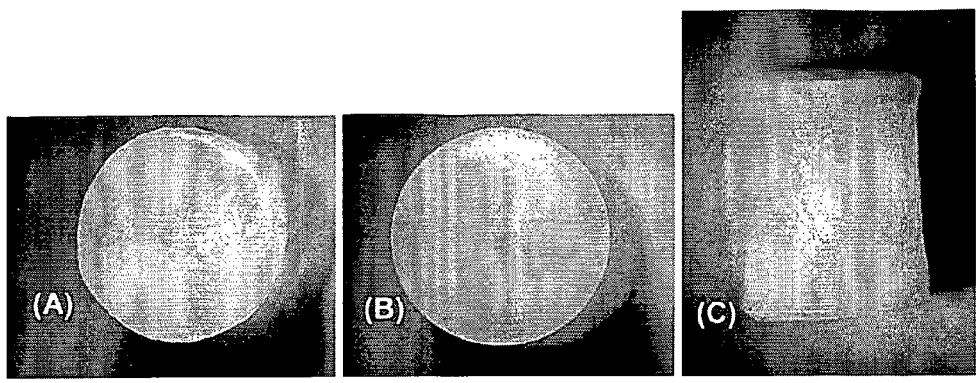
FIG. 13. Optical micrographs of a cylindrical hydrogel plug that is partially dehydrated in 100% PEG400 for insertion to the cavity; (A) top (B) bottom and (C) side view of the hydrogel plug.

FIG. 13 shows the cylindrical hydrogel plug ready for insertion into the cavity. The hydrogel plug was partially dehydrated (gravimetrically deswelled by 46% with respect to the initial as-gelled weight) after 100% PEG immersion.

Figure 14:
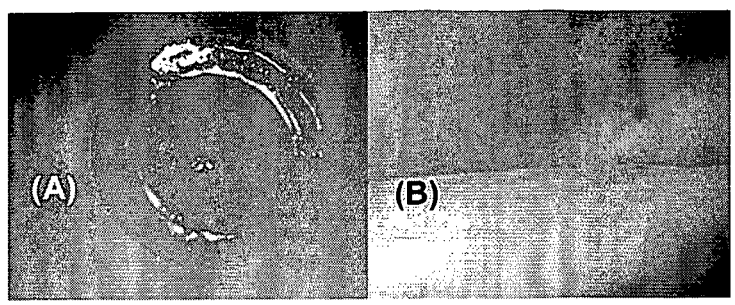
FIG. 14. Optical micrograph of the partially dehydrated hydrogel plug upon insertion into the cylindrical defect cavity of bovine knee cartilage; (A) top view and (B) side view.

FIG. 14 shows the hydrogel plug inserted in the cartilage cavity of bovine knee for POD test. Both top view and the side view show that the dimension of the inserted hydrogel plug well matched the dimension of the cavity. Note that the height of the hydrogel inside the cavity was about the same as that of the surrounding cartilage or minimally higher.

After hydrogel plug insertion, the cartilage specimens were mounted on the POD. The specimens were kept in bovine serum for about 1 hour with no motion or load, for re-hydration of the hydrogel plug prior to the POD run. At this time, another cylindrical hydrogel sample ("soak control") was placed in the same container, in order to measure the extent of reswelling (re-hydration) of the free floating, unconfined hydrogel plugs in bovine serum during the POD run.

Figure 15:
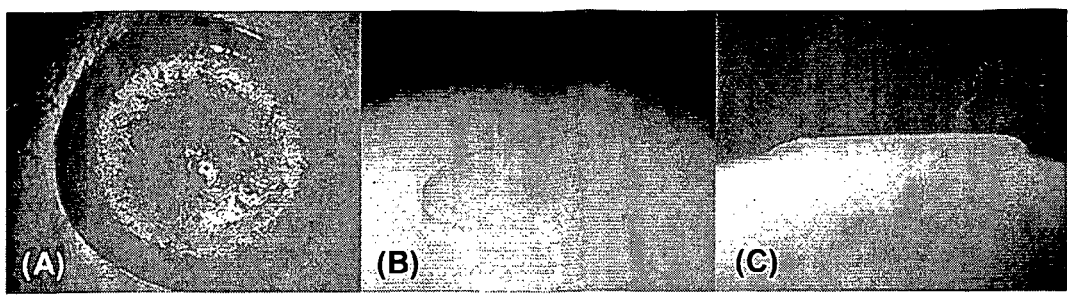
FIG. 15. Optical micrograph of the inserted hydrogel plug in a cylindrical defect cavity after 1-hour of re-hydration in serum prior to POD run; (A) top view (B) tilted top view and (C) side view. Note that the diameter and height of the inserted hydrogel plug have increased compared with FIG. 14.

The inserted hydrogel plug showed some swelling after 1 hour of exposure in serum, protruding slightly from the surrounding cartilage (see FIG. 15). Table 14 shows the dimensional change in the "soak-control" hydrogel cylinder that was immersed in the same serum bath as the cartilage setup during the POD runs. Similar to the inserted hydrogel plug in FIG. 15, the soak-control hydrogel plug showed reswelling presumably due to rapid re-hydration after 1 hour exposure to serum resulting in the recovery of over 94% of the fully re-hydrated equilibrium weight and dimension.

Figure 16:
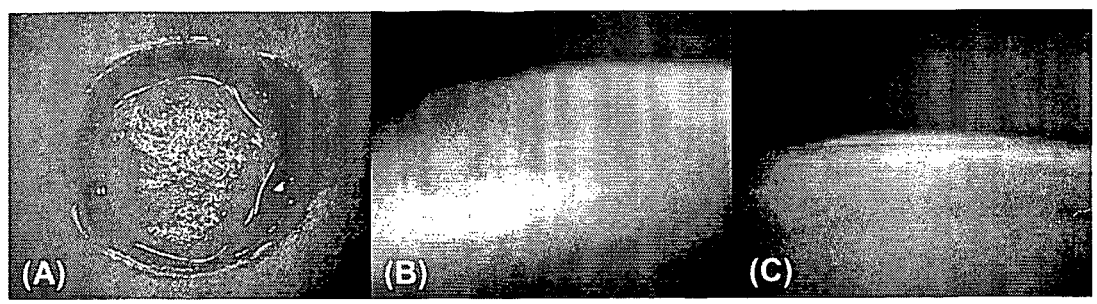
FIG. 16. Optical micrograph of the inserted hydrogel plug in a cylindrical defect cavity at 80,000 cycle POD runs; (A) top view (B) tilted top view and (C) side view.
Figure 17:
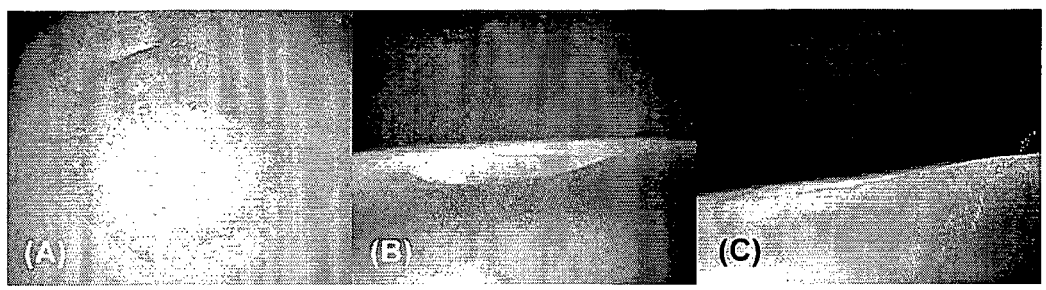
FIG. 17. Optical micrograph of the inserted hydrogel plug in a cylindrical defect cavity at 160,000 cycle POD runs; (A) top view (B) tilted top view and (C) side view.

After 80,000 cycles of articulating against the cartilage counter face, the hydrogel plug seated further inside the cartilage cavity, with a slight decrease in its height (FIG. 16). After space 160,000 cycles of POD runs, the plug was still stable, maintaining the same plug height as it had after 80,000 cycles. No visible wear or tear of the hydrogel plug was observed (see FIG. 17).

TABLE 13

Dimensional comparison of the hydrogel plug that was inserted in the cavity at each test step: (1) right after cutting from the "as-gelled" sheet, (2) after partial dehydration before insertion. (3) Dimension of the cavity defect is included for direct comparison with the hydrogel plug dimension.

| Dimensions | (1) Plug templated from the "as-gelled" sheet | (2) Partially dehydrated hydrogel plug before insertion to cavity | (3) Cavity |
|---|---|---|---|
| Diameter (mm) | 6.53 | 5.4 | ~5.2 |
| Height (mm) | 8.76 | 7.03 | ~6.7 |
| Weight (g) | 0.3104 | 0.1644 | — |

14. Immersion of PVA Hydrogel in 100% or 50% Aqueous PEG Solution Followed by Slow Annealing A hot PVA/PEG gelling solution was prepared as described Example 1 and poured into a hot mold (7 mm H×2.5 cm D×4.5 cm W) kept at 90° C., the mold was covered and insulated with an insulating blanket. The mold was left to cool down to room temperature to form a hydrogel. After 1 day of gelling at room temperature, the molded hydrogel sheet was cut into cylindrical hydrogels using a trephine blade (Diameter 9.5 mm) mounted on the drill press. Height, diameter and weight of each cylindrical hydrogel specimens were measured upon cutting, for "as-gelled" reference.

TABLE 14

Dimensional changes of the soak-control hydrogel plug that was free-floating in the POD serum container during the POD run: (1) right after cutting from the sheet, (2) after partial dehydration (3) after full re-hydration in serum during the POD run.

| Dimensions 1 | (1) Original cut hydrogel "as-gelled" | (2) Partially dehydrated hydrogel plug | (3) Partially re-hydrated hydrogel plug upon exposure to serum (1 hour) | (4) Fully re-hydrated hydrogel plug in serum (4 days) |
|---|---|---|---|---|
| Diameter (mm) | 6.38 | 5.3 | 6.14 | 6.22 |
| Height (mm) | 8.41 | 7.06 | 8.25 | 8.55 |
| Weight (g) | 0.2889 | 0.155 | 0.2476 | 0.2620 |

Some of the cylindrical hydrogels were immersed in 100% PEG400 liquid and some of the hydrogels were immersed in a 50% PEG400 aqueous solution at room temperature with agitation for 30 days. Immersion in 100% PEG400 or 50% PEG400 solution resulted in partial to complete removal of water from the hydrogel and hence partial or complete dehydration of the hydrogel.

Control Group with No Annealing:

The 100% PEG-immersed hydrogel specimens and 50% PEG-immersed specimens were separately placed in saline solution with agitation at room temperature for re-hydration and removal of PEG from the hydrogel for 6 days. The saline solution was replaced with fresh saline everyday during immersion. The final height, diameter and weight of the hydrogel specimens were recorded daily after blot-drying. Percent weight changes of the hydrogel after PEG dehydration and subsequent re-hydration in saline were calculated with respect to the "as-gelled" state. The gels were then further analyzed to determine the equilibrium water content as described in Example 2.

1-Hour Slow-Annealing Group:

The 100% PEG400-immersed gel specimens and 50% PEG400-immersed specimens were blot-dried and was annealed by heating from room temperature to 160° C. at approximately 5° C./min and subsequently keeping at 160° C. for a total annealing time of one hour (slow anneal). The height, diameter and weight of the gel specimens before and after annealing were recorded. After annealing, the specimens were immersed in saline solution with agitation at room temperature for re-hydration and removal of PEG from the hydrogel for 6 days. The saline solution was replaced with fresh saline everyday during immersion. The final height, diameter and weight of the gel specimens were recorded daily after blot-drying during re-hydration. Percent weight changes of the hydrogel after PEG dehydration, annealing and subsequent re-hydration in saline were calculated with respect to the "as-gelled" state. The gels were then further analyzed to determine the equilibrium water content as described in Example 2.

5-Hour Slow-Annealing Group:

The 100% PEG400-immersed hydrogel specimens and 50% PEG400-immersed specimens were blot-dried and slow-annealed from room temperature up to 160° C. for 1 hour and kept at 160° C. for 4 more hours. The height, diameter and weight of the gel specimens before and after annealing were recorded. After annealing, the gels were immersed in saline solution with agitation at room temperature for re-hydration and removal of PEG from the hydrogel for 6 days. The saline solution was replaced with fresh saline everyday during immersion. The final height, diameter and weight of the hydrogel specimens were recorded daily after blot-drying during re-hydration. Percent weight changes of the gel after PEG dehydration, annealing and subsequent re-hydration in saline were calculated with respect to the "as-gelled" state. The gels were then further analyzed to determine the equilibrium water content as described in Example 2.

The control group and the 1-hour and 5-hour slow-annealing groups all had reached equilibrium re-hydration in about 1 day of soaking in saline solution at room temperature.

TABLE 15

The weight percent change of the "as-gelled" PVA hydrogels at different steps of processing is shown*.

| | Equilibrium Weight Change (%) | |
|---|---|---|
| Measurements made | 50% PEG400 Group | 100% PEG400 Group |
| After equilibrium dehydration in respective PEG solutions | −29 | −40 |
| After equilibrium dehydration in respective PEG solutions followed by saline re-hydration | +2 (+31) | 0 (+40) |
| After PEG dehydration followed by 1 hour of slow annealing | −49 | −49 |
| After PEG dehydration followed by 5 hour of slow annealing | −51 (−20[a]) | −54 (−14[a]) |
| After PEG dehydration, 1 hour of slow annealing and equilibrium saline re-hydration | −33 | −20 |
| After PEG dehydration, 5 hour of slow annealing and equilibrium saline re-hydration | −32 (+19[b]) | −30 (+24[b]) |

*The total percent weight changes of the hydrogels at each step were calculated with respect to the "as-gelled" weight. For example, (−) sign denotes deswelling (loss of weight) from the original "as-gelled" state, whereas (+) sign denotes swelling (gain of weight) from the "as-gelled" state.
[a]Represents the percent weight change between PEG400 dehydration step and slow annealing step.
[b]Represents the percent weight change between the slow annealing step and equilibrium re-hydration in saline.

The hydrogel samples lost weight in the PEG400 solutions that is they deswelled as shown in the Table 15. The equilibrium weight loss was about 30% in 50% PEG400 solution and 40% in 100% PEG 400 solution. Slow annealing caused further weight loss. The 1-hour and 5-hour slow annealing caused the same amount of weight loss, approximately an additional 20%, resulting in a total weight loss of about 50% from the "as-gelled" weight. After annealing, both 1 hour- and 5 hour-annealed hydrogels that had been treated by immersion in 50% PEG400 re-hydrated to the same extent, which was only −35% of the "as-gelled" weight. On the other hand, the re-hydration in saline of the 50% PEG dehydrated control specimens (that were not slow-annealed) showed a much higher equilibrium re-hydration levels.

It is noted that after the slow-annealing process, the surface of the hydrogel specimens were slightly wet with residual PEG. Thus, the additional deswelling during slow-annealing includes the loss of PEG as well as loss of water.

Annealing after PEG dehydration can be used to fabricate hydrogel implants. The equilibrium re-hydration levels can be tailored based on the concentration of PEG solution used prior to the annealing step.

TABLE 16

Equilibrium water content of the As-Gelled 15-28 PVA-PEG hydrogels after various steps

| Sample | Equilibrium water content (%) |
|---|---|
| As-gelled and re-hydrated | 86.50 ± 0.011 |
| 100% PEG400 dehydration and re-hydration | 88.85 ± 0.207 |
| 100% PEG400 dehydration and followed by 1 hour slow annealing and re-hydration | 85.35 ± 0.755 |
| 100% PEG400 dehydration and followed by 5 hour flash annealing and re-hydration | 84.88 ± 0.347 |
| 50% PEG400 dehydration and re-hydration | 88.89 ± 0.517 |
| 50% PEG400 dehydration and followed by 1 hour slow annealing and re-hydration | 85.63 ± 2.969 |
| 50% PEG400 dehydration and followed by 5 hour flash annealing and re-hydration | 85.63 ± 3.290 |

Table 16 shows the equilibrium water content (EWC) of the as-gelled samples after various steps of processing described above. The PEG400 dehydration slightly increased the EWC. Both of the slow and flash annealing further decreased the EWC of the PEG400 dehydrated samples. The concentration of the PEG400 solution used during the dehydration step did not affect the EWC of the subsequently re-hydrated or annealed and then re-hydrated gels.

15. Dehydration and Re-Hydration of 5 Cycle Freeze-Thaw PEG-PVA Hydrogels

Thirty grams of poly (vinyl alcohol) (PVA, MW=115,000) were added to 170 grams of cold deionized water and stirred while heating for about 2 hours to prepare a fully dissolved 15% (wt) PVA solution. The dissolved PVA solution was kept in an air convection oven (DKN600, Yamato) at 90° C. for about 16 hours. Poly (ethylene glycol) (PEG, MW=400) was heated to 90° C. in an air convection oven.

52.88 grams of hot PEG (at approximately 90° C.) was slowly mixed with 160 grams of hot (at approximately 90° C.) PVA solution by mechanical stirring while heating. The mixture solution was then poured into a hot mold (7 mm H×25 mm D×45 mm W) and sealed with a cover to form a hydrogel sheet. The mold was then immediately placed in a −17° C. freezer for 16 hours, and taken out to room temperature for thawing for 8 hours. This completed one "freeze-thaw (FT)"

cycle. This freeze-thaw process was repeated up to five cycles to form 5-cycle freeze-thaw PVA-PEG hydrogels. Upon removal from the mold, the hydrogel sheet was cut into cylindrical samples using trephine blades (Diameter 6.5 mm). Height, diameter and weight of each cylindrical hydrogel specimens were measured upon cutting, for "as-freeze-thawed" reference. Note the hydrogel samples contained PVA, PEG, and water at this stage.

PEG-Dehydrated Group:

Some of the as-freeze-thawed cylindrical hydrogel specimens were immersed in 100% PEG400 liquid at room temperature with agitation for 7 days. Immersion in 100% PEG resulted in removal of water from the hydrogel. Subsequent to 7-day PEG400 immersion, the specimens were annealed in nitrogen at 160° C. by placing in an oven already heated to 160° C. for one hour (flash anneal). The annealed samples were then placed in saline solution at room temperature until equilibrium re-hydration was reached. Some of the PEG400 treated hydrogel samples were placed in saline for re-hydration with no annealing.

Vacuum-Dehydrated Group:

Some of the as-freeze-thawed cylindrical hydrogel specimens were dehydrated in vacuum at room temperature for 7 days. Vacuum dehydration resulted in dehydration of the hydrogel specimens. Subsequent to 7-day vacuum dehydration, the specimens were further dehydrated by flash annealing. The annealed samples were then placed in saline solution at room temperature until equilibrium re-hydration was reached. Some of the vacuum treated hydrogel samples were placed in saline for re-hydration with no annealing.

For both of the PEG-dehydrated and Vacuum-dehydrated groups of specimens, the height, diameter and weight of the gel specimens before and after annealing were recorded. Similarly, the specimens were immersed in saline solution with agitation at room temperature for re-hydration and removal of PEG from the hydrogel. The saline solution was daily replaced with fresh saline during immersion. The final height, diameter and weight of the gel specimens were daily recorded after blot-drying. Percent weight changes of the hydrogel after PEG dehydration, annealing and subsequent re-hydration in saline were calculated with respect to the "as-freeze-thawed" state.

The as-freeze-thawed gels swelled in saline solution by about 29%. This swelling was likely a result of PEG/water exchange between the gels and the saline solution. The as-freeze-thawed gels deswelled when immersed in PEG or placed in vacuum by about −21% and −60%, respectively. The extent of deswelling was much greater in vacuum than it was in PEG. When the deswollen gels were placed in saline for re-hydration, the equilibrium weight change from the as-freeze-thawed weight was 27 and 36% for the PEG and vacuum dehydrated specimens, respectively. The flash annealing did not affect the weight of the gels after vacuum dehydration; however, the PEG dehydrated gels deswelled to −43% form their as-freeze-thawed weights. Upon equilibrium re-hydration following the flash annealing, the PEG dehydrated samples showed more shrinkage (about −16%) with respect to the as-freeze-thawed weight than the vacuum dehydrated samples (about 0%). Therefore, a denser hydrogel can be obtained with the PEG dehydration than the vacuum dehydration when flash annealing is used with freeze-thawed PVA/PEG gels. These denser gels also were tougher than the less dense ones.

16. Dehydration and Re-Hydration of 5 Cycle Freeze-Thaw 15% PVA Hydrogels

Thirty grams of poly (vinyl alcohol) (PVA, MW=115,000) were added to 170 grams of cold deionized water and stirred while heating for about 2 hours to prepare a fully dissolved 15% (wt) PVA solution. The dissolved PVA solution was kept in an air convection oven (DKN600, Yamato) at 90° C. for about 16 hours.

The hot PVA solution was poured into a hot mold (7 mm H×25 mm D×45 mm W) and sealed with a cover to form a hydrogel sheet. The mold was then immediately placed in a −17° C. freezer for 16 hours, and taken out to room temperature for thawing for 8 hours. This completes one "freeze-thaw (FT)" cycle. This freeze-thaw process was repeated up to five cycles to form 5-cycle freeze-thaw 15% PVA hydrogels. Upon removal from the mold, the hydrogel sheet was cut into cylindrical hydrogels using trephine blades (Diameter 6.5 mm). Height, diameter and weight of each cylindrical hydrogel specimens were measured upon cutting, for "as-freeze-thawed" reference.

TABLE 17

The weight percent change of the 5 cycle freeze-thawed PVA-PEG hydrogels after different steps of processing is shown*.

| Measurement made | Percent weight change of as-freeze-thawed gels (%) |
|---|---|
| After equilibrium hydration in saline solution | 27.2 ± 0.01* |
| After PEG dehydration | −21.0 ± 5.6 |
| After PEG dehydration followed by equilibrium saline re-hydration | 26.9 ± 3.3 |
| After PEG dehydration followed by flash annealing | −42.5 ± 0.66 |
| After PEG dehydration followed by flash annealing followed by equilibrium saline re-hydration | −15.5 ± 0.8 |
| After vacuum dehydration | −60.4 ± 0.07 |
| After vacuum dehydration followed by equilibrium saline re-hydration | 36.2 ± 0.01 |
| After vacuum dehydration followed by flash annealing | −60.0 ± 0.01 |
| After vacuum dehydration followed by flash annealing followed by equilibrium saline re-hydration | −0.06 ± 0.01 |

*The total percent weight changes of the hydrogels at each step were calculated with respect to the "as-freeze-thawed" weight. The (−) sign denotes deswelling (loss of weight) from the original "freeze-thawed" state, whereas (+) sign denotes swelling (gain of weight) from the "freeze-thawed" state. Solid content or equilibrium water content (EWC) is necessary to compare to the following example (HSB).

PEG-Dehydrated Group:

Some of the as-freeze-thawed cylindrical hydrogel specimens were immersed in 100% PEG400 liquid at room temperature with agitation for 7 days. Immersion in 100% PEG resulted in removal of water from the hydrogel. Subsequent to 7-day PEG400 immersion, the specimens were annealed in nitrogen at 160° C. by placing in an oven already heated to 160° C. for one hour (flash anneal). The annealed samples were then placed in saline solution at room temperature until equilibrium re-hydration was reached. Some of the PEG400 treated hydrogel samples were placed in saline for re-hydration with no annealing.

Vacuum-Dehydrated Group:

Some of the as-freeze-thawed cylindrical hydrogel specimens were dehydrated in vacuum at room temperature for 7 days. Vacuum dehydration resulted in removal of water form the hydrogel specimens. Subsequent to 7-day vacuum dehydration, the specimens were further dehydrated by flash annealing. The annealed samples were then placed in saline solution at room temperature until equilibrium re-hydration was reached. Some of the vacuum treated hydrogel samples were placed in saline for re-hydration with no annealing.

For both of the PEG-dehydrated and Vacuum-dehydrated groups of specimens, the height, diameter and weight of the gel specimens before and after annealing were recorded. Similarly, the specimens were immersed in saline solution with agitation at room temperature for re-hydration and removal of PEG from the hydrogel. The saline solution was daily replaced with fresh saline during immersion. The final height, diameter and weight of the gel specimens were daily recorded after blot-drying. Percent weight changes of the hydrogel after PEG dehydration, annealing and subsequent re-hydration in saline were calculated with respect to the "as-freeze-thawed" state.

TABLE 18

The weight percent change of the 5 cycle freeze-thawed 15% PVA hydrogels after different steps of processing is shown*.

| Measurement made | Percent weight change of as-freeze-thawed gels (%) |
|---|---|
| After equilibrium hydration in saline solution | −15.8 ± 0.002 |
| After PEG dehydration | −74.95 ± 0.41 |
| After PEG dehydration followed by equilibrium saline re-hydration | −30.84 ± 1.6 |
| After PEG dehydration followed by flash annealing | −77.24 ± 0.61 |
| After PEG dehydration followed by flash annealing followed by equilibrium saline re-hydration | −62.84 ± 1.4 |
| After vacuum dehydration | −81.29 ± 0.003 |
| After vacuum dehydration followed by equilibrium saline re-hydration | −49.14 ± 0.006 |
| After vacuum dehydration followed by flash annealing | −81.32 ± 0.003 |
| After vacuum dehydration followed by flash annealing followed by equilibrium saline re-hydration | 2.15 ± 0.003 |

*The total percent weight changes of the hydrogels at each step were calculated with respect to the "as-freeze-thawed" weight. The (−) sign denotes deswelling (loss of weight) from the original "freeze-thawed" state, whereas (+) sign denotes swelling (gain of weight) from the "freeze-thawed" state.

The as-freeze-thawed gels deswelled in saline solution by about −16%. This deswelling was likely a result of continued curing of the gels; curing can increase the crosslink density of the gels and expel water. The as-freeze-thawed gels deswelled when immersed in PEG or placed in vacuum by about −75% and −81%, respectively. The extent of deswelling was much greater in vacuum than it was in PEG. When the deswollen gels were placed in saline for re-hydration, the equilibrium weight change from the as-freeze-thawed weight was −31 and −49% for the PEG and vacuum dehydrated specimens, respectively. The flash annealing did not affect the weight of the gels after neither of the two dehydration methods used. Upon equilibrium re-hydration following the flash annealing, the PEG dehydrated samples showed substantially more shrinkage (about −63%) with respect to the as-freeze-thawed weight than the vacuum dehydrated samples, which in fact showed a weight gain with respect to their as freeze-thawed weight (about 2%). Therefore, a denser hydrogel can be obtained with the PEG dehydration than one obtained with the vacuum dehydration when flash annealing is used with freeze-thawed PVA gels. These denser gels also were tougher than the less dense ones.

17. Effects of Presence of PEG on Biaxial Compression of PVA Hydrogel

Thirty grams of poly (vinyl alcohol) (PVA, MW=115,000) were added to 170 grams of cold deionized water and stirred while heating for about 2 hours to prepare a fully dissolved 15% (wt) PVA solution. The dissolved PVA solution was kept in an air convection oven (DKN600, Yamato) at 90° C. for about 16 hours. Poly (ethylene glycol) (PEG, MW=400) was heated to 90° C. in an air convection oven.

52.88 grams of hot PEG (at approximately 90° C.) was slowly mixed with 160 grams of hot (at approximately 90° C.) PVA solution by mechanical stirring while heating. The mixture solution was then poured into a hot (about 90° C.) mold of a rectangular prism shape (40 mm×45 mm×50 mm). The mold was left to cool down to room temperature under an insulating blanket over 24 hours. Two gel blocks were thus fabricated and their respective weights were recorded.

One of the gel blocks was used in its "as-gelled" state; therefore it contained PEG. The other one was first immersed in saline solution with agitation for removal of PEG and to reach equilibrium hydration for 1 day. This block was denoted as "dePEGed" gel. The weight of the dePEGed gel block was measured. The two blocks were then deformed under uniaxial compression.

The gel blocks were then separately deformed by placing between two flat platens that were attached to an MTS machine (MiniBionix). The deformation was uniaxial. The compression proceeded at a rate of 0.2 mm/min until a compression ratio of 10 (ratio of initial to final height) was reached. When the compression ratio of 10 was reached, the displacement was held constant for at least 24 hours until equilibrium stress relaxation. Both of the deformed gels were weighed. After uniaxial compression, both of the deformed gels were immersed in saline solution until equilibrium re-hydration. The gels were weighed again in their re-hydrated state. The percent weight changes of the gels form their "as-gelled" states were calculated at different steps of processing.

Upon completion of uniaxial compression, dimension of rectangular prism shaped "as-gelled" hydrogel specimen was changed from a length of 41.83 mm, a width of 47.37 mm and a height of 49.75 mm in its as-gelled form, to a length of 88.29 mm, a width of 98.74 mm, and a height of 6.4 mm. In the case of dePEGed hydrogel, specimen dimension changed from a length of 43.49 mm, a width of 50.01 mm, and a height of 53.03 mm from the dePEGed state to a length of 93.17, a width of 97.78, and a height of 6.71 following the deformation step.

When the deformed gels were re-hydrated in saline, the "as-gelled" specimen, which was compressed in the presence of PEG, exhibited a more anisotropic reswelling than the "dePEGed" specimen, which was compressed in the absence of PEG.

TABLE 19

The weight percent change of the dePEGed or as-gelled PVA-PEG hydrogels at different steps of processing*.

| | Percent weight change (%) | |
|---|---|---|
| Measurement made | As-gelled | dePEGed |
| Before uniaxial compression | 0.00 | 13.1 |
| After uniaxial compression | −48.5 | −62.5 |
| After equilibrium hydration in saline solution | −8.1 | −50.2 |

*The total percent weight changes of the hydrogels at each step were calculated with respect to the "as-gelled" weight. The (−) sign denotes deswelling (loss of weight) from the original "as-gelled" state, whereas (+) sign denotes swelling (gain of weight) from the "as-gelled" state.

Table 19 shows the percent weight change of the gels at different steps of fabrication. The dePEGed gel gained about 13% weight during the dePEGing process, likely a result of the water/PEG exchange in the gel and additional swelling of the gel in the absence of PEG with increased water uptake. Uniaxial compression induced weight loss in the gel samples, which is attributed to elution of water and/or PEG from the gels. The weight loss was larger with the dePEGed gel than the as-gelled one, as the former contained more water; this also indicates that water is the primary ingredient being expelled from the gels during deformation. Following the subsequent re-hydration in saline, the as-gelled gel showed an overall 8% weight loss from its as-gelled state, in contrast with a 50% loss for the dePEGed sample. Therefore, if the deformation is carried in the presence of a large molecule, such as PEG (400 g/mol), the gel has a higher hydration capacity than it was when it is deformed in the absence of any large molecules. It is speculated that the large molecules remain in the porous structure of the gel during deformation and prevent their collapse; as a result, water uptake into these protected pores is possible even after a large strain plastic deformation. On the other hand, when the large molecule is not present, water is squeezed out of the pores during deformation and thus the pores are collapsed. During the subsequent re-hydration step the ability of the deformed gel to rehydrate is substantially reduced because of the decreased number of pores available for water absorption.

It is also shown above in other examples that the large molecules protect the pores from collapsing during high temperature annealing, allowing better re-hydration capacity to the gels.

One can either start with hydrogels containing large molecules, like PEG, or impregnate the hydrogel with a large molecule to improve its re-hydration capacity following any type of deformation. This can be especially useful if one needs to maximize the water content in an oriented hydrogel.

18. The Effect of PEG Presence During Freeze-Thaw

15% PVA solution was prepared dissolving PVA in deionized water at 90° C. while stirring continuously. Resulting solution was centrifuged to remove air bubbles and poured into a heated rectangular glass mold (45 mm by 70 mm by 7 mm) kept at around 90° C. The mold was covered by a glass cover kept at 90° C. and the mold was sandwiched between two 20 mm thick stainless steel blocks that were also kept at 90° C. The sandwiched mold was immediately placed in to a −20° C. freezer and was kept there for 16 hours for a freeze cycle. Subsequently the sandwiched mold was taken out of the freezer and was left to heat up to room temperature for the first thaw cycle. The freezing and thawing was repeated 4 more times to obtain a total of 5 freeze-thaw cycles. These gels are denoted as FT-PVA.

The 5-freeze-thaw method was performed with a PVA starting solution containing PEG. A hot 15-28 PVA/PEG gelling solution was prepared as described in Example 1. Resulting solution was treated as described above to obtain a five times freeze-thaw processed PVA/PEG hydrogel. These gels are denoted as FT-PVA/PEG.

Both of the freeze-thaw gels were each cut into 30 cylindrical samples (total of 60) with a 6.5 mm trephine blade. The samples were immersed into individual vials containing saline (0.9% NaCl in water) to investigate the dissolution behavior of 5×FT 15% PVA gels. For 10 days three samples of both group were removed at regular intervals from the saline and placed in an air convection oven at 90° C. until equilibrium dehydration was reached, which was confirmed gravimetrically. The solid content (PVA only for the PVA freeze-thaw gel and PVA and PEG for the PVA/PEG freeze-thaw gel) was determined gravimetrically by dividing the dry weight of the hydrogel by its hydrated weight.

The effect of vacuum dehydration duration on the re-hydration ability of FT-PVA was also investigated. Six cylindrical samples of FT-PVA were placed in vacuum at room temperature. Three of the samples were removed from the vacuum after one day and the remaining three after 5 days. All samples were immersed in saline right after vacuum dehydration to achieve equilibrium re-hydration, which was confirmed gravimetrically. The FT-PVA/PEG hydrogel samples were only subjected to 5-day vacuum dehydration followed by re-hydration.

In addition, the effect of annealing on the FT-PVA and FT-PVA/PEG was investigated. Three cylindrical samples of each FT-PVA and FT-PVA/PEG were first dehydrated under vacuum at room temperature for 5 days and subsequently annealed under nitrogen atmosphere by placing into an oven already heated to 160° C. for one hour (flash annealing). The weight change of the samples was determined after vacuum dehydration and again after annealing. Following annealing, all samples were re-hydrated in saline for at least 5 days. Finally, the equilibrium water content (EWC) of these samples was determined using the method outlined in Example 2.

TABLE 20

Shows the weight changes after various processing steps.

| The FT-PVA samples after | Weight Change (%) | EWC (%) |
|---|---|---|
| 1 day vacuum dehydration | −78.26 ± 0.0013 | Not measured |
| 1 day vacuum dehydration and re-hydration | −46.21 ± 0.0026 | Not measured |
| 5 days vacuum dehydration | −81.29 ± 0.0025 | Not measured |
| 5 days vacuum dehydration and re-hydration | −49.15 ± 0.0056 | 66.9 ± 0.004 |
| 5 days vacuum dehydration, followed by flash annealing | −81.35 ± 0.0026 | Not measured |
| 5 days vacuum dehydration, followed by flash annealing and subsequent re-hydration | 2.15 ± 0.0027 | 48.35 ± 0.014 |

TABLE 21

Shows the weight changes after various processing steps.

| The FT-PVA/PEG samples after | Weight Change of (%) | EWC of (%) |
|---|---|---|
| 1 day vacuum dehydration | −58.43 ± 0.0024 | Not measured |
| 1 day Vacuum dehydration and re-hydration | 35.22 ± 0.0017 | Not measured |
| 5 days vacuum dehydration | −60.38 ± 0.0017 | Not measured |
| 5 days vacuum dehydration and re-hydration | 36.21 ± 0.011 | 91.4 ± 0.011 |
| 5 days vacuum dehydration, followed by flash annealing | −60.55 ± 0.0055 | Not measured |
| 5 days vacuum dehydration, followed by flash annealing and subsequent re-hydration | 0.21 ± 0.0054 | 83.36 ± 0.0019 |

The average weight of the hydrated FT-PVA samples decreased during storage in saline. This was previously attributed to dissolution of PVA in saline. But the PVA content measurements showed no measurable change over the 10 day period, suggesting that the FT-PVA gel continued to cure, that is crystallized, during saline storage, hence expelling water and having an appearance of loosing weight. The FT-PVA/PEG gels, on the other hand, showed a weight gain during saline storage. It is expected for the PEG to diffuse out of and water to diffuse into the samples during saline storage. Likely, the water uptake was larger than PEG loss, which amounted to an apparent weight increase with the FT-PVA-PEG samples.

Tables 20-21 show the weight changes after various processing steps. The duration of vacuum did not substantially affect the extent of dehydration of the gels, indicating that 1 day vacuum dehydration was sufficient to reach equilibrium with these size samples. Flash annealing did not affect the weight of the vacuum dehydrated gels. The FT-PVA/PEG gels showed less weight loss upon vacuum dehydration than the FT-PVA samples. The same was true for the subsequent flash annealing step. The FT-PVA/PEG gels re-hydrated more than the FT-PVA gels. The EWC of the vacuum dehydrated, flash annealed, and re-hydrated FT-PVA/PEG was higher than that of the FT-PVA. The EWC of the FT-PVA/PEG after dePEG-ing and re-hydration in saline was 86%; the vacuum dehydration and subsequent flash annealing reduced the EWC of FT-PVA/PEG to only 83%. The EWC of the FT-PVA was 81% and decreased to 48% upon vacuum dehydration and subsequent annealing forming a very tough, elastic and transparent gel.

19. Deformation of PEG-Dehydrated PVA/PEG Gel to 75% Uniaxial Compression

A PVA/PEG gel was prepared in a cylindrical shape as described in Example 1 and was poured in a hot mold (diameter 44 mm×height 40 mm) maintained at about 90° C. The mold was cooled down to room temperature under an insulating blanket to form an as-gelled hydrogel. The hydrogel was removed from the mold and placed in 100% PEG with agitation for dehydration for 3 hours prior to deformation. The hydrogel was subsequently deformed in a Carver Hydraulic Press. The initial gel height was 37 mm and the final gel height after deformation was 5 mm. After the deformation step, the gel was immersed in 100% PEG for 24 hours with agitation and subsequently was re-hydrated in saline solution with agitation. After re-hydration, the final gel height of the deformed gel sample was about 10 mm. The total deformation ratio from the initial gel height at the as-gelled state to that of the final gel height following re-hydration after deformation was about 75%.

20. Improved In-Plane Stiffness by Deformation

The deformed gel prepared in Example 19 was characterized using an MTS machine to determine its compressive deformation behavior in comparison with an undeformed control gel. The thickness of the 75% deformed gel specimen was about 10 mm. The control gel specimen was prepared by gelling a hot 15/28 PVA-PEG mixture solution in a mold to obtain a 10 mm thin sheet. Both of the deformed and undeformed gels cut to obtain a square block shaped test sample (16 mm×17 mm×10 mm). The test samples were placed in saline at 37° C. for 1 day; and were then individually tested on the MTS machine. The test samples were placed between two flat metal platens and compressed at a rate of 10 mm/min. Load needed to maintain the constant deformation rate was acquired as a function of displacement.

Figure 18:
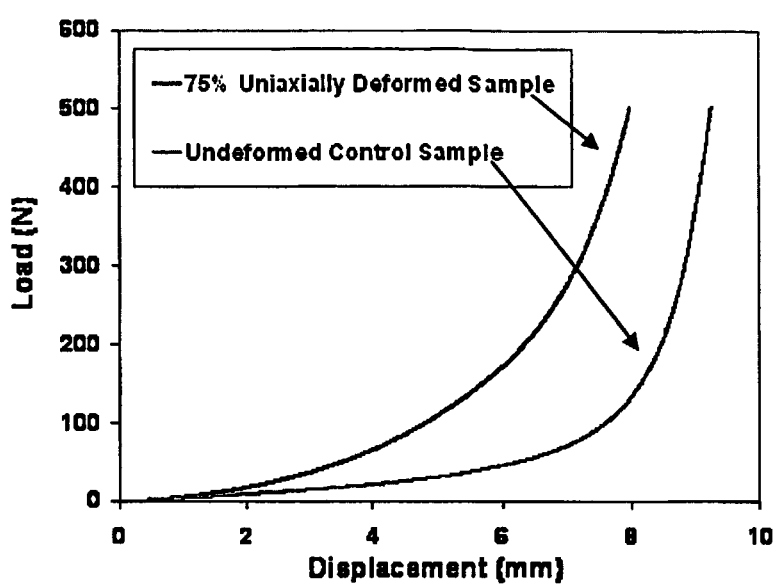
FIG. 18. Load vs. displacement curves for a dePEGed PVA/PEG gel and a dePEGed PVA/PEG gel that was subjected to 75% uniaxial deformation.

FIG. 18 shows the load displacement behavior of the deformed and undeformed test samples. The deformed test sample showed a stiffer deformation behavior than the undeformed test sample. At a given load level the undeformed control hydrogel showed substantially higher displacements than the previously deformed hydrogel. One can increase the stiffness of any hydrogel by applying permanent deformation. Higher levels of deformation can result in higher stiffness.

21. Creep Behavior of Hydrogels

Hydrogel samples form the above examples were machined with a 16 mm diameter trephine and were allowed to equilibrate in saline solution at 40° C. for at least 24 hours prior to the start of the creep test. Some of the examples included here were irradiated prior to the trephine machining. Prior to irradiation the hydrogel sheets were placed in saline and they were irradiated in saline solution. The irradiation was carried out using a 2.5 MeV Van de Graaf generator. Either 25 kGy or 100 kGy radiation dose was applied to the hydrogel sheets. Trephine machining was carried out after irradiation to prepare the creep samples.

The hydrogel creep test was done on a MTS (Eden Prairie, Minn.) 858 Mini Bionix servohydraulic machine. Cylindrical hydrogel specimens, approximately 16 mm in diameter and between 5-10 mm in height, were placed between stainless steel compression plates for testing. Prior to the start of the test, the top and bottom compression plates were brought together and the LVDT displacement was zeroed at this position. After placing the specimen on the bottom plate, the top plate was lowered until it made contact with the top surface of the creep specimen. The displacement reading from the LVDT on the MTS was recorded as the height of the specimen.

TABLE 22

Shows the elastic and viscoplastic strains achieved during the loading and unloading stages of the creep experiments with the hydrogel samples used in this example.

| # | Sample (all samples were hydrated in saline at room temperature to achieve equilibrium hydration levels and then conditioned in 40° C. saline for at least 24 hours prior to testing) | Strain on Initial Loading (%) | Total Strain after 10 hours of Loading (%) | Viscoelastic Strain after 10 hours of Loading (%) | Elastic Recovery on Unloading (%) | Viscoelastic Strain Recovery after 10 hours of Unloading (%) | Total Strain Recovery after 10 hours of Unloading (%) | Total Strain after 10 hours of Loading followed by 10 hours of Unloading (%) |
|---|---|---|---|---|---|---|---|---|
| 1 | 15% PVA + 5 times freeze thaw (Example 18) | 30.7 | 38.2 | 7.5 | 19.1 | 5.3 | 24.4 | 13.9 |
| 2 | 15-28 PVA/PEG + 5 times freeze thaw (Example 15) | 50.1 | 79.4 | 29.3 | 6.0 | 4.4 | 10.4 | 69.0 |
| 3 | 15-28 PVA/PEG + 1 time freeze thaw (similar to Example 15 except only one time freeze-thaw) | 54.2 | 80.0 | 25.8 | 6.3 | 3.0 | 9.3 | 70.6 |
| 4 | 15-28 PVA/PEG + DePEGed + deformed to compression ratio of 10 in the channel-die + dehydrated in 100% PEG400 (Example 5) | 33.5 | 55.2 | 21.7 | 10.2 | 6.0 | 16.2 | 39.0 |

TABLE 22-continued

Shows the elastic and viscoplastic strains achieved during the loading and unloading stages of the creep experiments with the hydrogel samples used in this example.

| # | Sample (all samples were hydrated in saline at room temperature to achieve equilibrium hydration levels and then conditioned in 40° C. saline for at least 24 hours prior to testing) | Strain on Initial Loading (%) | Total Strain after 10 hours of Loading (%) | Viscoelastic Strain after 10 hours of Loading (%) | Elastic Recovery on Unloading (%) | Viscoelastic Strain Recovery after 10 hours of Unloading (%) | Total Strain Recovery after 10 hours of Unloading (%) | Total Strain after 10 hours of Loading followed by 10 hours of Unloading (%) |
|---|---|---|---|---|---|---|---|---|
| 5 | 15-28 PVA/PEG + DePEGed + deformed to compression ratio of 10 in the channel-die + vacuum dehydrated + flash annealed (Example 5) | 17.9 | 31.2 | 13.3 | 1.8 | 6.2 | 8.0 | 23.2 |
| 6 | 15-28 PVA/PEG as-gelled + vacuum dehydrated + flash anneal + dePEGed (Example 9) | 12.0 | 42.3 | 30.3 | 5.3 | 17.0 | 22.3 | 20.1 |
| 7 | 20-28 PVA/PEG + DePEGed (Similar to Example 1 but starting with 20% PVA solution) | 45.3 | 65.1 | 19.8 | 15.7 | 3.2 | 18.9 | 46.2 |
| 8 | 15-28 PVA/PEG + DePEGed | 59.7 | 79.2 | 19.5 | 11.1 | 0.7 | 11.8 | 67.3 |
| 9 | 15-28 PVA/PEG + DePEGed + e-beam irradiated to 25 kGy in saline solution | 51.2 | 76.1 | 24.8 | 10.9 | 2.7 | 13.6 | 62.4 |
| 10 | 15-28 PVA/PEG + DePEGed + e-beam irradiated to 100 kGy in saline solution | 37.8 | 71.4 | 33.5 | 5.7 | 16.5 | 22.2 | 49.2 |
| 11 | 15-28 PVA/PEG as-gelled (Example 1) | 51.1 | 75.2 | 24.1 | 7.2 | 5.8 | 13.0 | 62.2 |
| 12 | 15-28 PVA/PEG as-gelled + e-beam irradiated to 100 kGy in saline solution | 56.8 | 78.4 | 21.6 | 10.4 | 1.1 | 11.5 | 66.9 |
| 13 | 15-28 PVA/PEG as-gelled + dehydrated in 50% PEG + e-beam irradiated to 100 kGy | 42.9 | 73.2 | 30.3 | 1.1 | 2.4 | 3.5 | 69.6 |
| 14 | 15-28 PVA/PEG as-gelled + slow annealed | 32.5 | 70.4 | 38.0 | 4.6 | 11.3 | 15.9 | 54.6 |
| 15 | 15-28 PVA/PEG as-gelled + fast annealed | 12.1 | 46.2 | 34.1 | 3.3 | 22.0 | 25.3 | 20.9 |

The compressive load was initially ramped at a rate of 50 N/min to a creep load of 100N. This load was maintained constant for 10 hours. The load was subsequently reduced at a rate of 50 N/min to a recovery load of 10 N. This load was also held constant for 10 hours. Time, displacement and load values were recorded once every 2 seconds during the loading and unloading cycles. The data was plotted as compressive strain vs. time to compare the creep behavior of different hydrogel formulations described above (see FIG. 19).

With this example, it is demonstrated that the creep resistance of PVA hydrogels can be improved by a number of methods. For instance, radiation crosslinking increased the creep resistance of the PVA hydrogel. Similarly, previous permanent deformation imparted by the channel-die increased the creep resistance of the PVA hydrogel. The effect of vacuum dehydration followed by annealing was also an increase in the creep resistance. One can use any number of these methods in a number of combinations to tailor the creep resistance of the hydrogel.

22. The Effect of Multiple Loading/Unloading on Creep Resistance

Two hydrogel samples were used in this example. One sample was 15/28 PVA/PEG gel that was dePEGed and equilibrated in saline solution (Example 1). The other sample was 15/28 PVA/PEG gel that was first dePEGed, then deformed to a compression ratio of 10 in the channel-die, subsequently dehydrated in 100% PEG400, and finally equilibrated in saline solution. Both sheets had a thickness of about 10 mm.

The dePEGed PVA hydrogel sheet was machined with a 16 mm trephine to obtain a cylindrical test sample. The test sample was placed in 40° C. saline for at least 24 hours prior to testing. Subsequently, the cylindrical test sample was placed in an MTS machine between two metal plates submerged in 40° C. saline. The MTS machine applied 100 N of constant load for 10 hours followed by a reduction of the load to 10 N and maintenance of a 10 N constant load for an additional 10 hours. This entire cycle constituted one loading/unloading cycle and was identical to the one described in Example 21. The loading/unloading cycles were repeated 3 times. During the loading/unloading cycles, the extent of deformation of the cylindrical hydrogel was measured on the MTS machine as a function of time.

Figure 20:
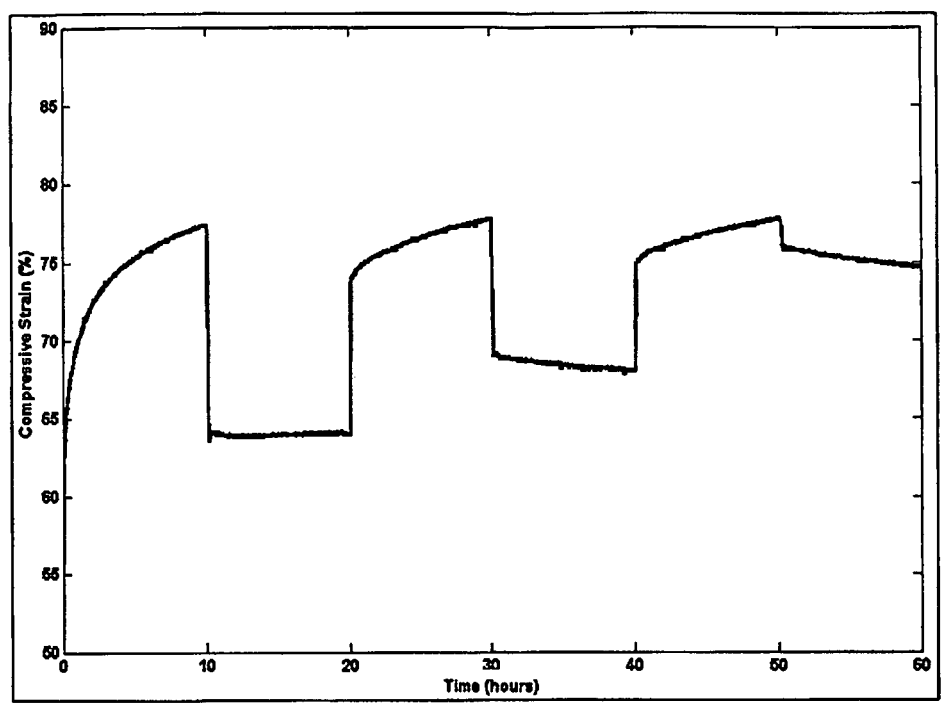
FIG. 20. Variation of compressive strain with time during multiple creep deformation and recovery cycles for a 15-28 PVA/PEG gel that was dePEGed and equilibrated in saline solution.

FIG. 20 shows the compressive strain as a function of time during the three-loading/unloading cycles. During the first loading cycle, upon application of the 100 N of load, there was a large elastic deformation of about 59.5%. This was followed by a viscoplastic deformation over the course of the 10 hours of constant load reaching a total deformation level of 77.4%. At the completion of the 10 hours, when the load was reduced down to 10 N, there was an elastic recovery of 13.4%, which brought the overall deformation to approximately 64%. In the subsequent 10-hour unloading cycle, there was almost no recovery of the creep deformation.

The multiple cycles of loading and unloading were used to creep the hydrogel samples in order to increase their creep resistance. When the loading and unloading cycles were repeated, the extent of creep deformation during the subsequent loading cycles decreased indicating that the creep resistance of the material increased. One can use this method to improve the creep resistance of hydrogels for applications in interpositional devices. For instance, one can deform a large block of hydrogel under multiple loading/unloading cycles between two shaped metal plates so as to obtain a near net shaped implant with improved creep resistance. Alternatively, one can deform a large block of hydrogel between two metal plates by subjecting it to multiple loading and unloading cycles to improve its creep resistance. The deformed hydrogel can then be machined into the shape of the desired implant. The implant can be packaged and sterilized.

Figure 21:
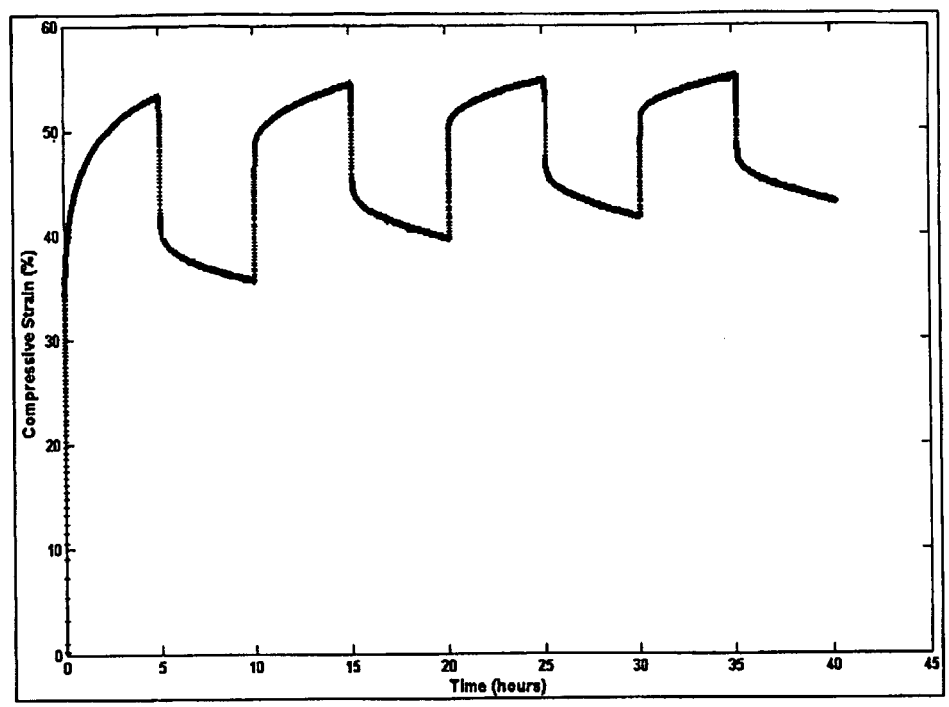
FIG. 21. Variation of compressive strain with time during multiple creep deformation and recovery cycles for a 15-28 PVA/PEG gel that was first dePEGed, then deformed to a compression ratio of 10 in a channel-die and subsequently dehydrated in 100% PEG400.

The above method of multiple loading/unloading was repeated on a 15/28 PVA/PEG gel that was first dePEGed, then deformed to a compression ratio of 10 in a channel-die subsequently dehydrated in 100% PEG400 and finally equilibrated in saline solution. The loading/unloading cycles were identical except with shorter durations of each (5 hour of loading and 5 hour of unloading). This sample also showed an increase in its creep resistance with an increasing number of loading/unloading cycles. (FIG. 21)

23. Packaging and Sterilization of the PVA Medical Device

The gel medical devices described in the examples presented here are packaged in saline solution and sterilized. The sterilization is achieved by gamma radiation. In some embodiments, the gamma sterilization is used to both sterilize the packaged device and also to crosslink the gel medical device. In the instances where a high crosslink density is desirable a high radiation dose (above 40 kGy) is used.

Alternatively, the gel medical devices are fabricated from sterile components in a clean room, packaged in sterile saline solution, therefore require no further sterilization.

Alternatively, the gel medical devices are packaged in gas permeable packages, sterilized using gas plasma or ethylene oxide, and subsequently placed in sterile saline solution in a clean room and packaged for shipping.

The saline solution used in the above alternate methods of packaging can be replaced with 100% PEG or a PEG/water mixture to achieve different levels of dehydration in the gel medical devices. The gel medical device is shipped in a full or partial dehydrated state. Upon insertion into the body rehydration occurs and the gel medical device swells to partially or completely fill the space that it is placed in (such as the knee joint, hip joint, shoulder joint, etc.).

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

We claim:

1. A method of making a tough hydrogel, the method comprising:
    (a) heating a polymeric material and a gellant and mixing the heated polymeric material with the heated gellant to form a gelling solution having a temperature above room temperature and cooling the gelling solution to room temperature thereby forming an as-gelled hydrogel, the gellant being a non-solvent for the hydrogel;
    (b) annealing the as-gelled hydrogel by heating to a temperature that is below the melting point of the as-gelled hydrogel that is being annealed, wherein the non-solvent gellant remains in the as-gelled hydrogel during annealing and prevents collapse of porosity in the as-gelled hydrogel; and
    (c) cooling the heated as-gelled hydrogel to room temperature, thereby forming a tough hydrogel,
    wherein the gellant comprises polyethylene glycol.

2. The method according to claim 1, wherein the as-gelled hydrogel is annealed in air, an inert gas, or under vacuum.

3. The method of claim 1, wherein prior to the annealing step (b), the as-gelled hydrogel is dehydrated by one or more methods selected from the group consisting of:
    (i) air-drying the as-gelled hydrogel at room temperature,
    (ii) heating the as-gelled hydrogel to a temperature below the melting point of the as-gelled hydrogel, and
    (iii) placing the as-gelled hydrogel under vacuum.

4. The method of claim 3 further comprising re-hydrating the dehydrated hydrogel by placing the dehydrated hydrogel in:
    water, saline solution, Ringer's solution, buffer solution,
    or in a humid chamber, wherein the placing is performed at room temperature or at an elevated temperature that is below the melting point of the as-gelled hydrogel.

5. The method according to claim 1, wherein the non-solvent gellant is subsequently removed from the as-gelled hydrogel after annealing.

6. The method according to claim 5, wherein the non-solvent gellant is removed from the as-gelled hydrogel by:
    (i) immersing the as-gelled hydrogel in water, organic solvents, or salt solutions, or
    (ii) placing the as-gelled hydrogel in a supercritical fluid.

7. The method according to claim 1, wherein the polymeric material is polyvinyl alcohol (PVA), a copolymer of PVA, or a blend of PVA with another polymer.

8. The method according to claim 1, wherein the as-gelled hydrogel is deformed at a temperature that is below the melting point of the as-gelled hydrogel before and/or after annealing.

9. A tough hydrogel made by the method according to claim 1.

10. A medical implant comprising the tough hydrogel according to claim 9.

11. The medical implant according to claim 10 which is further sterilized by radiation sterilization, gas plasma sterilization, or ethylene oxide sterilization.

12. The medical implant of claim 10 which is an interpositional device or a mosaicplasty plug.

13. The medical implant of claim 12, wherein the interpositional device is a unispacer, wherein the unispacer is a free floating articular implant in a human joint.

14. The medical implant of claim 13, wherein the human joint is a knee, a hip, a shoulder, an elbow, or an upper or a lower extremity joint.

* * * * *